United States Patent
Haynes et al.

(10) Patent No.: US 10,588,960 B2
(45) Date of Patent: *Mar. 17, 2020

(54) LIPOSOME-PEPTIDE CONJUGATE AND METHOD OF USING SAME TO INDUCE PRODUCTION OF ANTI-HIV ANTIBODIES

(71) Applicant: Duke University, Durham, NC (US)

(72) Inventors: Barton F. Haynes, Durham, NC (US); S. Munir Alam, Durham, NC (US); Hua-Xin Liao, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,487

(22) Filed: Jun. 26, 2017

(65) Prior Publication Data
US 2018/0161423 A1 Jun. 14, 2018

Related U.S. Application Data

(60) Continuation of application No. 15/195,841, filed on Jun. 28, 2016, now Pat. No. 9,717,789, which is a division of application No. 11/785,077, filed on Apr. 13, 2007, now Pat. No. 9,402,893, which is a continuation-in-part of application No. PCT/US2006/013684, filed on Apr. 12, 2006.

(60) Provisional application No. 60/757,478, filed on Jan. 10, 2006, provisional application No. 60/697,997, filed on Jul. 12, 2005, provisional application No. 60/675,091, filed on Apr. 27, 2005, provisional application No. 60/670,243, filed on Apr. 12, 2005.

(51) Int. Cl.

| | |
|---|---|
| *A61K 39/21* | (2006.01) |
| *A61K 39/385* | (2006.01) |
| *A61K 39/00* | (2006.01) |
| *A61K 39/12* | (2006.01) |
| *C07K 16/10* | (2006.01) |
| *C07K 16/18* | (2006.01) |
| *C12N 7/00* | (2006.01) |
| *A61K 9/127* | (2006.01) |
| *C07K 14/005* | (2006.01) |

(52) U.S. Cl.
CPC .............. *A61K 39/21* (2013.01); *A61K 9/127* (2013.01); *A61K 39/0005* (2013.01); *A61K 39/12* (2013.01); *A61K 39/385* (2013.01); *C07K 14/005* (2013.01); *C07K 16/1063* (2013.01); *C07K 16/18* (2013.01); *C12N 7/00* (2013.01); *A61K 2039/55505* (2013.01); *A61K 2039/55555* (2013.01); *A61K 2039/55561* (2013.01); *A61K 2039/55566* (2013.01); *A61K 2039/57* (2013.01); *A61K 2039/6018* (2013.01); *C07K 2317/76* (2013.01); *C07K 2319/00* (2013.01); *C12N 2740/16011* (2013.01); *C12N 2740/16111* (2013.01); *C12N 2740/16122* (2013.01); *C12N 2740/16134* (2013.01); *Y02A 50/41* (2018.01)

(58) Field of Classification Search
CPC .................... A61K 39/21; A61K 9/127; A61K 2039/55555; A61K 2039/6018; C12N 7/00; C12N 2740/16122; C12N 2740/16134

See application file for complete search history.

(56) References Cited

U.S. PATENT DOCUMENTS

| | | | |
|---|---|---|---|
| 4,994,440 A | 2/1991 | Creaven | |
| 5,693,752 A | 12/1997 | Katinger et al. | |
| 5,707,626 A | 1/1998 | Douvas et al. | |
| 5,756,674 A | 5/1998 | Katinger et al. | |
| 5,831,034 A | 11/1998 | Katinger et al. | |
| 5,866,694 A | 2/1999 | Katinger et al. | |
| 5,910,306 A | 6/1999 | Alving et al. | |
| 5,916,588 A | 6/1999 | Popescu et al. | |
| 5,919,459 A | 7/1999 | Nacy et al. | |
| 6,156,337 A | 12/2000 | Barenholz et al. | |
| 6,300,308 B1 | 10/2001 | Schroit | |
| 6,761,888 B1 | 7/2004 | Schenk | |
| 6,806,354 B2 | 10/2004 | Schroit | |
| 7,195,768 B2 | 3/2007 | Haynes et al. | |
| 7,459,165 B2 | 12/2008 | Charland et al. | |
| 9,402,893 B2 * | 8/2016 | Haynes | ............... A61K 39/0005 |
| 9,402,917 B2 * | 8/2016 | Alam | ............... A61K 47/48815 |
| 10,076,567 B2 * | 9/2018 | Haynes | .................. A61K 39/21 |
| 2001/0036461 A1 | 11/2001 | Haynes et al. | |
| 2004/0131610 A1 | 7/2004 | Thorpe et al. | |
| 2004/0131621 A1 | 7/2004 | Thorpe et al. | |
| 2004/0131622 A1 | 7/2004 | Thorpe et al. | |
| 2004/0161429 A1 | 8/2004 | Thorpe et al. | |

(Continued)

FOREIGN PATENT DOCUMENTS

| | | |
|---|---|---|
| CA | 2548483 A1 | 3/2005 |
| WO | WO-1995/0004524 A1 | 2/1995 |

(Continued)

OTHER PUBLICATIONS

Grundner, C., et al., Apr. 2002, Solid-Phase Proteoliposomes Containing Human Immunodeficiency Virus Envelope Glycoproteins, J. Virol. 76(7):3511-3521.*

(Continued)

*Primary Examiner* — Jeffrey S Parkin
(74) *Attorney, Agent, or Firm* — Wilmer Cutler Pickering Hale and Dorr LLP

(57) ABSTRACT

The present invention relates, in general, to human immunodeficiency virus (HIV), and, in particular, to a method of inducing neutralizing antibodies to HIV and to compounds and compositions suitable for use in such a method.

16 Claims, 21 Drawing Sheets

Specification includes a Sequence Listing.

(56) References Cited

U.S. PATENT DOCUMENTS

| | | |
|---|---|---|
| 2004/0213779 A1 | 10/2004 | Thorpe et al. |
| 2004/0241641 A1 | 12/2004 | Stiegler et al. |
| 2004/0265367 A1 | 12/2004 | Thorpe et al. |
| 2005/0025761 A1 | 2/2005 | Thorpe et al. |
| 2005/0080240 A1 | 4/2005 | Kunert et al. |
| 2005/0095282 A1 | 5/2005 | Schroit |
| 2006/0089326 A1 | 4/2006 | Krieg et al. |
| 2008/0031890 A1 | 2/2008 | Haynes et al. |
| 2008/0057075 A1 | 3/2008 | Haynes |
| 2009/0035360 A1 | 2/2009 | Lemoine |
| 2009/0220536 A1 | 9/2009 | Ofek et al. |
| 2010/0028415 A1 | 2/2010 | Haynes et al. |
| 2010/0047331 A1 | 2/2010 | Haynes et al. |
| 2012/0070488 A1 | 3/2012 | Haynes et al. |
| 2012/0128758 A1 | 5/2012 | Alam et al. |
| 2012/0183597 A1 | 7/2012 | Haynes et al. |
| 2013/0323299 A1 | 12/2013 | Haynes et al. |

FOREIGN PATENT DOCUMENTS

| | | | |
|---|---|---|---|
| WO | WO-1995/0007354 A1 | 3/1995 | |
| WO | WO-1995/0025124 A1 | 9/1995 | |
| WO | WO-1996/0033219 A1 | 10/1996 | |
| WO | WO-1996/0040243 A1 | 12/1996 | |
| WO | WO-1999/0033522 A2 | 7/1999 | |
| WO | WO-2000/0016746 A2 | 3/2000 | |
| WO | WO-2003/0022879 A2 | 3/2003 | |
| WO | WO-2003/0059953 A2 | 7/2003 | |
| WO | WO-2004/0006847 A2 | 1/2004 | |
| WO | WO-2004/0087738 A2 | 10/2004 | |
| WO | WO-2005/021574 A2 | 3/2005 | |
| WO | WO-2006/0110831 A2 | 10/2006 | |
| WO | WO-2008/0127651 A1 | 10/2008 | |
| WO | WO-20090111304 A2 | 9/2009 | |
| WO | WO-20100042942 A2 | 4/2010 | |
| WO | WO-2010/0114629 A2 | 10/2010 | |
| WO | WO-2012/0139097 A2 | 10/2012 | |

OTHER PUBLICATIONS

Aguilar et al., "Phospholipid Membranes Form Specific Nonbilayer Molecular Arrangements That Are Antigenic", The Journal of Biological Chemistry, vol. 274, No. 36, 1999, pp. 25193-25196.

Alam et al, "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes", The Journal of Immunology 178: 4424-4435 (2007).

Alam et al, "Role of HIV membrane in neutralization by two broadly neutralizing antibodies", PNAS 106(48): 20234-20239 (2009).

Alving et al, "HIV-1 lipid rafts, and antibodies to liposomes: implications for anti-viral-neutralizing antibodies (Review)", Molecular Membrane Biology 23(6): 453-465 (2006).

Alving, Carl R., "Immunologic aspects of liposomes: presentation and processing of liposomal protein and phospholipid antigens", Biochimica Biophysica Acta 1113: 307-322 (1992).

Alving, C. R., et al., "Preparation and Use of Liposomes in Immunological Studies," Liposome Technology, 2nd Edition, vol. III, pp. 317-343, 29 pages (1993).

Armbruster et al, "Passive immunization with the anti-HIV-1 human monoclonal antibody (hMab) 4E10 and hMab combination 4E10/ 2F5/2G12", Journal of Antimicrobial Chemotherapy 54: 915-920 (2004).

Barbato, G., et al., 2003, Structural analysis of the epitope of the anti-HIV antibody 2F5 sheds light into its mechanism of neutralization and HIV fusion, J. Mol. Biol. 330: 1101-1115.

Barthel and Wallace, "False-Positive Human Immunodeficiency Virus Testing in Patients With Lupus Erythematosus", Seminars in Arthritis and Rheumatism 23(1): 1-7 (1993).

Bate, et al, "Phospholipids coupled to a carrier induce IgG antibody that blocks tumour necrosis factor induction by toxic malaria antigens", Immunology 78: 138-145 (1993).

Brown et al, "Monoclonal Antibodies to Phosphatidylinositol Phosphate Neutralize Human Immunodeficiency Virus Type 1: Role of Phosphate-Binding Subsites", Journal of Virology 81(4): 2087-2091 (2007).

Callahan et al, "Phosphatidylserine on HIV Envelope Is a Cofactor for Infection of Monocytic Cells", The Journal of Immunology 170: 4840-4845 (2003).

Cardoso et al, "Broadly Neutralizing Anti-HIV Antibody 4E10 Recognizes a Helical Conformation of a Highly Conserved Fusion-Associated Motif in gp41", Immunity 22: 163-173 (2005).

Chang et al, "Immunogenicity of synthetic HIV-1 V3 loop peptides by MPL adjuvanted pH-sensitive liposomes", Vaccine 17: 1540-1548 (1999).

Chen et al, "Novel recombinant engineered gp41 N-terminal heptad repeat trimers and their potential as anti-HIV-1 therapeutics or microbicides", The Journal of Biological Chemistry 285(33): 25506-25515 (2010).

Chukwuocha et al, "Molecular and genetic characterizations of five pathogenic and two non-pathogenic monoclonal antiphospholipid antibodies", Molecular Immunology 39: 299-311 (2002).

Cornet et al, "Virosomes reconstituted from human immunodeficiency virus proteins and lipids", Biochem. Biophys. Res. Comm. 167(1): 222-231 (1990).

Creaven et al, "Initial Clinical Trial of Muramyl Tripeptide Derivative (MTP-PE) Encapsulated in Liposomes: An Interim Report", Abstract, Accession No. 90657770 CancerLit (1990).

Darland-Ransom et al, "Role of C. elegans TAT-1 Protein in Maintaining Plasma Membrane Phosphatidylserine Asymmemetry", Science 320: 528-531 (2008).

Del Papa et al, "Human beta2-Glycoprotein I Binds to Endothelial Cells Through a Cluster of Lysine Residues That Are Critical for anionic Phospholipid Binding and Offers Epitopes for anti-beta2-Glycoprotein I Antibodies", The Journal of Immunology 160:5572-5578 (1998).

Dennison et al, "Stable Docking of Neutralizing Human Immunodeficiency Virus Type 1 gp41 Membrane-Proximal External Region Monoclonal Antibodies 2F5 and 4E10 Is Dependent on the Membrane Immersion Depth of Their Epitope Regions", Journal of Virology 83(19): 10211-10223 (2009).

Douvas and Takehana, "Cross-Reactivity between Autoimmune Anti-U1 snRNP Antibodies and Neutralizing Epitopes of HIV-1 gp120/41", AIDS Research and Human Retroviruses 10(3): 253-262 (1994).

Douvas et al, "Neutralization of HIV Type 1 Infectivity by Serum Antibodies from a Subset of Autoimmune Patients with Mixed Connective Tissue Disease", AIDS Research and Human Retroviruses 12(16); 1509-1517 (1996).

Fairn and Grinstein, "A One-Sided Signal", Science 320: 458-460 (2008).

Frey et al, "A fusion-intermediate state of HIV-1 gp41 targeted by broadly neutralizing antibodies", PNAS 105(10): 3739-3744 (2008).

Frisch et al, "Synthetic Peptide-Based Highly Immunogenic Liposomal Constructs", Methods in Enzymology 373: 51-73 (2003).

Gomara et al, "Hexapeptides that interfere with HIV-1 fusion peptide activity in liposomes block GP41-mediated membrane fusion", FEBS letters 580: 2561-2566 (2006).

Hammel et al, "Mechanism of the Interaction of beta2-Glycoprotein I with Negatively Charged Phospholipid Membranes", Biochemistry 40: 14173-14181 (2001).

Haynes et al, "Cardiolipin Polyspecific Autoreactivity in Two Broadly Neutralizing HIV-1 Antibodies", Science 308: 1906-1908 (2005).

Huang et al, "A Monoclonal Antibody that Binds Anionic Phospholipids on Tumor Blood Vessels Enhances the Antitumor Effect of Docetaxel on Human Breast Tumors in Mice", Cancer Res. 65(10) 4408-4416 (2005).

Huang et al, "Anti-Tumor Effects and Lack of Side Effects in Mice of Immunotoxin Directed Against Human and Mouse Prostate-Specific Membrane Antigen", The Prostate 61: 1-11 (2004).

Huarte, N. et al., "The broadly neutralizing anti-human immunodeficiency virus type 1 4E10 monoclonal antibody is better adapted to membrane-bound epitope recognition and blocking than 2F5",

(56) References Cited

OTHER PUBLICATIONS

Journal of Virology, vol. 82, No. 18, p. 8986-8996, Sep. 2008, 4 pages of supplemental material (15 pages total).
Hunt and Krilis, "The Fifth Domain of beta2-Glycoprotein I Contains a Phospholipid Binding Site (Cys281-Cys288) and a Region Recognized by Anticardiolipin antibodies", Journal of Immunology 152: 653-659 (1994).
Ichikawa, et al, "Activation of APCs Through CD40 or Troll-like Receptor 9 Overcomes Tolerance and Precipitates Autoimmune Disease", The Journal of Immunology 169: 2781-2787 (2002).
International Search Report dated Jul. 31, 2008—International Appln No. PCT/US06/13684.
International Search Report for PCT/US2008/004709 dated Sep. 17, 2008.
Jiang et al, "Synthetic vaccines: the role of adjuvants in immune targeting", Current Medicinal Chemistry 10(15): 1423-1439 (2003)—Medline, Abstract, PMID: 12871139.
Kim M, et al. "immunogenicity of recombinant human immunodeficiency virus type 1-like particles expressing Igp41 derivatives in a pre-fusion state" Vaccine. Jun. 28, 2007;25(27):5102-14. Epub Oct. 9, 2006, 24 pages.
Kim, M., et al., "Immunogenicity of recombinant human immunodeficiency virus type 1-like particles expressing gp41 derivatives in a pre-fusion state," Vaccine, vol. 25, No. 27, pp. 5102-5114, 24 pages (Jun. 28, 2007).
Lenz et al, "Trimeric membrane-anchored gp41 inhibits HIV membrane fusion", J. Biol. Chem. 280(6): 4095-4101 (2005).
Letvin and Walker, Immunopathogenesis and immunotherapy in Aids virus infections, Nature Medicine 9(7): 861-866 (2003).
Liao et al, "A Group M Consensus Envelope Glycoprotein Induces Antibodies That Neutralize Subsets of Subtype B and C HIV-1 Primary Viruses", Virology 353(2): 268-282 (2006).
Lopez and Schnaar, "Determination of Glycolipid-Protein Interaction Specificity", Methods in Enzymology 417: 205-220 (2006).
Lorizate et al, "Recognition and Blocking of HIV-1 gp41 Pretransmembrane Sequence by Monoclonal 4E10 Antibody in a Raft-like Membrane Environment", The Journal of Biological Chemistry 281(51): 39598-39606 (2006).
Lu et al, "Identification of Polyclonal and Monoclonal Antibodies Against Tissue Plasminogen Activator in the Antiphospholipid Syndrome", Arthritis & Rheumatism 52(12): 4018-4027 (2005).
Luo et al, "Induction of neutralizing antibody against human immunodeficiency virus type 1 (HIV-1) by immunization with gp41 membrane-proximal external region (MPER) fused with porcine endogenous retrovirus (PERV) p15e fragment", Vaccine 24(4): 435-442 (2006).
Luster et al, "Plasma Protein beta-2-Glycoprotein 1 Mediates Interaction between the Anti-tumor Monoclonal Antibody 3G4 and Anionic Phospholipids on Endothelial Cells", The Journal of Biological Chemistry 281(40): 29863-29871 (2006).
Maksyutov et al, "Exclusion of HIV epitope shared with human proteins in prerequisite for designing safer AIDS vaccines", Journal of Clinical Virology 31S: S26-S38 (2004).
McGaughey, G. B., et al., "HIV-1 Vaccine Development: Constrained Peptide Immunogens Show Improved Binding to the Anti-HIV-1 gp41 MAb," Biochemistry, vol. 42, pp. 3214-3223 (2003).
Mercer and Helenius, "Vaccinia Virus Uses Macropinocytosis and Apoptotic Mimicry to Enter Host Cells", Science 320: 531-535 (2008).
Montefiori, "Neutralizing antibodies take a swipe at HIV in vivo", Nature Medicine 11(6): 593-594 (2005).
Muster et al, "Cross-Neutralizing Activity against Divergent Human Immunodeficiency Virus Type 1 Isolates Induced by the gp41 Sequence ELDKWAS", Journal of Virology 68(6): 4031-4034 (1994).
Nabel, "Close to the Edge: Neutralizing the HIV-1 Envelope", Science 308: 1878-1879 (2005).
Ofek et al, "Structure and Mechanistic Analysis of the Anti-Human Immunodeficiency Virus Type 1 Antibody 2F5 in Complex with Its gp41 Epitope", Journal of Virology 78(19): 10724-10737 (2004).

Perelson et al, "HIV-1 Dynamics in Vivo: Virion Clearance Rate, Infected Cell Life-Span, and Viral Generation Time", Science 271: 1582-1586 (1996).
Petrovas et al, "Anti-phospholipid Antibodies in HIV Infection and SLE With or Without Anti-phospholipid Syndrome: Comparisons of Phospholipid Specificity, Avidity and Reactivity with beta2-GPI", Journal of Autoimmunity 13: 347-355 (1999).
Pinto et al, "Panel of Anti-gp120 Monoclonal Antibodies Reacts with Same Nuclear Proteins in Uninfected Cells as Those Recognized by Autoantibodies from Patients with Systemic Lupus Erythematous", AIDS Research and Human Retroviruses 10(7): 823-828 (1994).
Putscher, M., et al., "Restricted antigenic variability of the epitope recognized by the neutralizing gp41 antibody 2F5," AIDS, vol. 10, No. 6, pp. 587-593 (Jun. 1996).
Ran et al, "Antitumor Effects of a Monoclonal Antibody that Binds Anionic Phospholipids on the Surface of Tumor Blood Vessels in Mice", Clinical Cancer Research 11: 1551-1562 (2005).
Ran et al, "Increased Exposure of Anionic Phospholipids on the Surface of Tumor Blood Vessels", Cancer Research 62: 6132-6140 (2002).
Rao, M., et al., "Immunostimulatory CpG motifs induce CTL responses to HIV type I oligomeric gpl140 envelope protein," Immunology and Cell Biology, vol. 82, pp. 523-530 (2004).
Rauch and Janoff, "Phospholipid in the hexagonal II phase is immunogenic: Evidence for immunorecognition of nonbilayer lipid phases in vivo", Proc. Natl. Acad. Sci. USA 87: 4112-4114 (1990).
Richards, R. L., et al., "Liposomes Containing Lipid a Serve as an Adjuvant for Induction of Antibody and Cytotoxic T-Cell Responses against RTS,S Malaria Antigen," Infection and Immunity, vol. 66, No. 6, pp. 2859-2865 (Jun. 1998).
Sakaue et al, "HIV Mucosal Vaccine: Nasal Immunization with gp 160-Encapsualted Hemagglutinating Virus of Japan-Liposome Induces Antigen-Specific CTLs and Neutralizing Antibody Responses", The Journal of Immunology 170: 495-502 (2003).
Sanchez-Martinez, S., et al., 2006, Membrane association and epitope recognition by HIV-1 neutralizing anti-gp41 2F5 and 4E1 0 antibodies, AIDS Res. Human Retrovir. 22(10):998-1006.
Scherer et al, "Difficulties in eliciting broadly neutralizing anti-HIV antibodies are not explained by cardiopin autoreactivity", AIDS 21(16): 2131-2139 (2007)—Medline, Abstract, PMID: 18090039.
Schnaar, "Isolation of Glycosphingolipids", Methods in Enzymology 230: 348-370 (1994).
Supplementary European Search Report dated Aug. 13, 2010 issued in connection with EP Appln. No. 06 74 0904.
Singh et al, "Reactivity profiles of broadly neutralizing anti-HIV-1 antibodies are distinct from those of pathogenic autoantibodies", AIDS 25: 1247-1257 (2011).
Stiegler and Katinger, "Therapeutic potential of neutralizing antibodies in the treatment of HIV-1 infection", Journal of Antimicrobial Chemotherapy 51: 757-759 (2003).
Stults et al, "Glycosphingolipids: Structure, biological Source, and Properties", Methods in Enzymology 179: 167-214 (1989).
Sullards et al, "Structure-Specific Quantitative Methods for Analysis of Sphingolipids by Liquid Chromatography-Tandem Mass Spectrometry: "Inside-Out" Sphingolipidomics", Chapter Four, Methods in Enzymology 432: 83-115 (2007).
Thorpe, "Vascular Targeting Agents as Cancer Therapeutics", Clinical Cancer Research 10: 415-427 (2004).
Trkola et al, "Delay of HIV-1 rebound after cessation of antiretroviral therapy through passive transfer of human neutralizing antibodies", Nature Medicine 11(6): 615-622, Epub May 8, 2005, Abstract, PMID: 15880120.
Vcelar et al. "Reassessment of autoreactivity of the broadly neutralizing HIV antibodies 4E10 and 2F5 and retrospective analysis of clinical safety data", AIDS 21: 2161-2170 (2007)—Abstract.
Vega-Ostertag et al, "A human monoclonal antiprothrombin antibody is thrombogenic in vivo and upregulates expression of tissue factor and E-selectin on endothelial cells", British Journal of Hematology 135: 214-219 (2006).
Vogel, "The role of adjuvants in retroviral vaccines", International Journal of Immunopharmacology 17(2): 85-90 (1995)—Medline, Abstract, PMID: 7657411.

(56) References Cited

OTHER PUBLICATIONS

Wang and Krieg, "Induction of autoantibody production but not autoimmune disease in HEL transgenic mice vaccinated with HEL in combination with CpG or control oligodeoxynucleotides", Vaccine 22: 2641-2650 (2004).
Wassef, N. M., et al., "Liposomes as Carriers for Vaccines," Immunomethods, vol. 4, pp. 214-222 (1994).
Wel et al, "Viral dynamics in human immunodeficiency virus type 1 infection", Nature 373: 117-122 (1995).
White et al, "Antibody and cytotoxic T-lymphocyte responses to a single liposome-associated peptide antigen", Vaccine 13(12): 1111-1122 (19995)—Medline, Abstract, PMID 7491819.
Written Opinion for PCT/US2008/004709 dated Sep. 17, 2008.
Ziegler and Stites, "Hypothesis: AIDS Is an Autoimmune Disease Directed at the Immune System and Triggered by a Lymphotropic Retrovirus", Clinical Immunology and Immunopathology 41: 305-313 (1986).
Zhu et al, Characterization of IgG monoclonal anti-cardiolipin/anti-beta2GP1 antibodies from two patients with antiphospholipid syndrome reveals three species of antibodies, British Journal of Hematology 105: 102-109 (1999).
Zwick et al, "Anti-Human Immunodeficiency Virus Type 1 (HIV-1) Antibodies 2F5 and 4E10 Require Surprisingly Few Crucial Residues in the Membrane-Proximal External Region of Glycoprotein gp41 to Neutralize HIV-1", Journal of Virology 79(2): 1252-1261 (2005).
Zwick et al, "The Long Third Complementarity-Determining Region of the Heavy Chain is Important in the Activity of the Broadly Neutralizing Anti-Human Immunodeficiency Virus Type 1 Antibody 2F5", Journal of Virology 78(6): 3155-3161 (2004).
Zwick, Michael B., "The membrane-proximal external region of HIV-1 gp41: a vaccine target worth exploring," AIDS, vol. 19, pp. 1725-1737 (2005).

\* cited by examiner

Broadly Neutralizing Antibodies (2F5, 4E10) bind to epitopes that lie proximal to the host membrane
- Against epitopes that lie within HIV-1 gp41 (aa 660-683) membrane proximal external region (MPER)
- 2F5 -ELDKWAS; 4E10-WFNITNW
- Both IgG3s; Long hydrophobic CDR3s

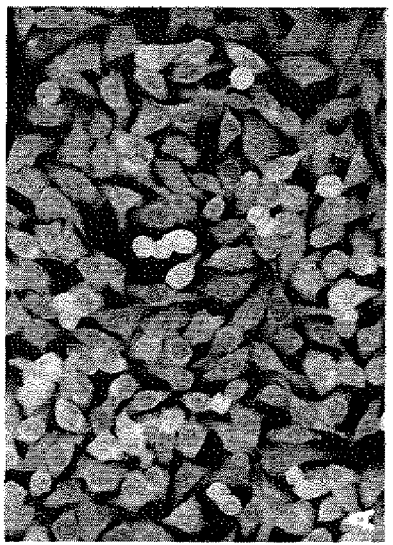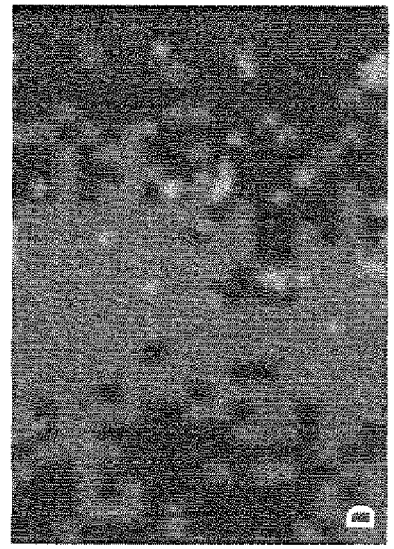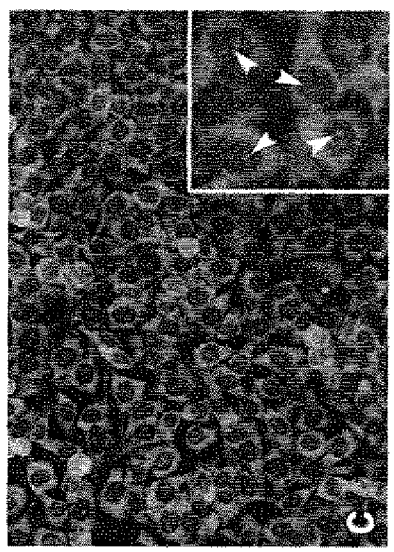

Amino Acid and Nucleotide Sequences of CON-S Env gp160*

MRVRGIQRNCQHLWRWGTLILGMLMICSAAENLWVTVYYGVPVWKEANTLFCASDAKAYDTEVHNVWATHACVPTDPNPQEIVLENVTENFNMWKNMVEQMHEDII
SLWDQSLKPCVKLTPLCVTLNCTNVNVTNTTNNTEEKGEIKNCSFNITTEIRDKKQKVYALFYRLDVVPIDDNNNNSSNYRLINCNTSAITQACPKVSFEPIPIHYCA
PAGFAILKCNDKKFNGTGPCKNVSTVQCTHGIKPVVSTQLLLNGSLAEEEIIRSENITNNAKTIIVQLNESVEINCTRPNNNTRKSIRIGPGQAFYATGDIIGDIRQ
AHCNISGTKWNKTLQQVAKKLREHFNNKTIIFKPSSGGDLEITTHSFNCRGEFFYCNTSGLFNSTWIGNGTKNNNNTNDTITLPCRIKQIINMWQGVGQAMYAPPIEG
KITCKSNITGLLLTRDGGNNNTNETEIFRPGGGDMRDNWRSELYKYKVVKIEPLGVAPTKAKRRVVEREKRAVGIGAVFLGFLGAAGSTMGAASITLTVQARQLLSGI
VQQQSNLLRAIEAQQHLLQLTVWGIKQLQARVLAVERYLKDQQLLGIWGCSGKLICTTTVPWNSSWSNKSQDEIWDNMTWMEWEREINNYTDIIYSLIEESQNQEKN
EQELLALDKWASLWNWFDITNWLWYIKIFIMIVGGLIGLRIVFAVLSIVNRVROGYSPLSFQTLIPNPRGPDRPEGIEEEGGEQDRDRSIRLVNGFLALAWDDLRSLC
*LFSYHRLRDFILIAARTVELLGRKGLRRGWEALKYLWNLLQYWGQELKNSAISLLDTTAIAVAEGTDRVIEVVQRACRAILNIPRRIRQGLERALL*

*Cleavage site and fusion domain are in italic font and underlined; the immunodominant region is highlighted in bold. The transmembrane and cytoplasmic domains are underlined.

Figure 4A

Nucleotide sequence:
ATGGCGGTGCGCGGGCATCCAGCGCAACTGCCAGCACCTGTGGCGCTGGGCACCCTGATCCTGGGCATGCTGCTGATGATCGCTCTCCGCCCCGAGAACCTGTGGGTGACC
GTGTACTAGGCGTGCCCCGTGTGGAAGGAGGCCAACACCACCCTGTTCTGCGCCGAGGTGCTGCCTACGACACCGAGGTGCACAACGTGTGGCCACCCAGCC
TGCGTGCCACCGACCCCAACCCCAGAGAGATCGTGTGGAGAACTTCAACATGGTGAGCAGATCCACGAGGACATCATC
TCCCTGTGGACCAGTCCCTGAAGCCCTGCGTGAAGCTGACCCCTGTGCGTGAACTGCACCAACGTGAACGTGACCAACAACACCGAGGAG
AAGGGCGAGATCAAGAACTGCTCCTTCAACATCACCGAGATCCGCCAGGAAGCAGAAGGTGTACGCCCTGTTCTACGGCCATGCGCCGCC
AACAACAACAACACTCCTCCAACTGCCTGATCAACTGCGCACACCTCCGCCATCACCCCAGGTGTCCTTCGAGCCATCCCATCCTACTGCGCC
CCCGCCGGCTTCGCCATCTGCTGTGCCACCCGCCCAACAACAAGAAGTTCAAGGACAAGAAGTGTCCACCGTGCACCTGCCATCAAGCCCGTGTG
TCCACCCAGTCGCTGCCCTGGAACGGCTCCCTGGAGGAGAGATCATCATCGCTCCGAGGAGAACATTACCAACGCCAAGAACATCATCGTGCAGTGAACGAGTCC
GTGGAGATCAACTGCACCCGCCCCAACAACAACAACACCCGCAAGTCCAATCGCCTTCTACGCCAGGCCTTCTACCGCCGACATCCGCCAG
GCCCACTGCAACATCTCCGGCACCAAGTGGAACAAGACCCTGCGCGAACCAGCCTGCGAGAGCTGCCAACACACCTCCCGGCTGTTCAACTGGCAACGGCACCAAG
GGCGGGACTGGAGATCACCACCACCCACCATCACCCGCTGCTGACCGCGTGTTACGCCGGATCCCAGGCCCATGTACGCCCCCCCCATCGAGGC
AACAACAACAACACCGACACCATCAACATCACCGGACGGCGGCAACAACAACACCGAGAGACCACCAAGCCCGTGTGGAGCCGCCAGAAGCGCCC
AAGATCACCTGCAAGTCCGAGCTGCTCAACCGGTCGTGTTCCTGGGCCTTCCTGGGCCTGTACAAGGTGTGAAGATCAAGGGTGTGAAGATCGAGCCCTCCACCATGGGCCCTGACCCCGAGCCCCGAGTCGCCCGAGTCCGGCATC
GTGGGCATCGGCCTCGTGCCGCCCAACTGCTGGCGCCCCAGCCCGGCCCGAGCGCCGCCATCAGCAGCTGCAGCTGAGCTGCAGCTCCGGGCATCGTGTGCAGCTGACCTGCAAGTCCCTGGGGCATCGTGCCCACCACCGTGACCCTGCAGCC
CGCTACCCTGAAGGACAGTCCAACTGCGCTGCCCGGCATCTGCTGGACCTGGAACTCCTTCCTGGTCCAACAAGTCCCAGGAC
GAGATCTGGACGACAACATGTGGCCTGATGAGTGGAGTGGGACCCTGGCCCTCCCTGTGAACTGGTTCGACATCACCAACTGGTGGTACATCAAGATCTTCATCATGATCGTGGGCGGCCTG
GAGCAGGAGCTGTGGCCCTGGAGGACAGTGGGCCCCTCCCATGTGCTGTGCCGTGCTGCCCGTGTGGTGCTACCTCCCCTGATCGTGGAACCGCGTGAACCTGCCTCAGACCCGGGCCCCGAC
ATCGGCCTGGCCATCGTGTTCGCCGTCGTGCTGTCCATCGTGAACGCGCGCAGGACGGGCTCCCAGGCTACCTCCCCTGGTAACGGCCTCCATCGCCGTGGAACGGCCTGCCGCTCCGTGC
CGCCGAGGCATCGAGGAGGAGGGCCTGCCGCAGCTGAAGCCGCCCATCGAGCGGAGCTGTGGACACCACGCCCATGCCGCCCGGGAGGCCTGGAGGCCCTGAAGTACCTTG
CTGTTCTCCTACCAGCCATCGCCCGCGCAGTGCTGCAGTACTGGGCCGCCATCCCGCCCGATGCGCCGCCGCCGCCATGCGCCATCCCGCCCATCCCGCCCCATCGAGAACTGCTG
TGGAACCTGCCGCGCTACTGGGCCCATCCTGCCGCCGAGTCAGGAGCTGAAGAACATCCCCGCCCAGGGCTGGAGCCTGCCATGCGCCGTGGAGAACCGTGGCACGGCGTGATCGAGGTG
GTGCAGGAGCCTGCGCCCTGCTGCCCGCCCATCCCGCCGCATCCCCGCCCAGGGCTGGAGCCTGCCCCTGCTGTAA

Figure 4B

| Phospholipid | Structure | Phase | Neutralization Titer (Geometric Mean) HIV-1 SF162 |
|---|---|---|---|
| Cardiolipin | 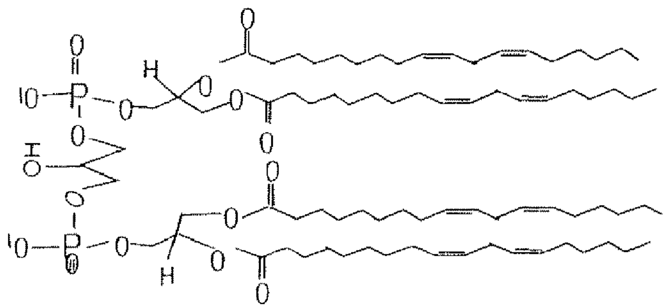 | Lamellar | <20 |
| | | Hexagonal$_{II}$ | <20 |
| POPS | 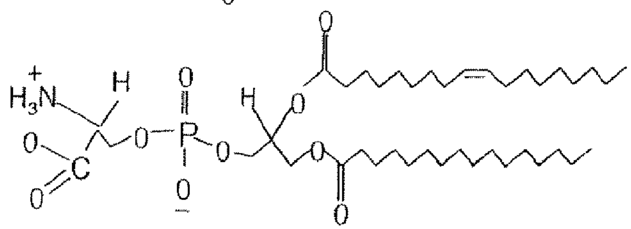 | Lamellar | <20 |
| | | Hexagonal$_{II}$ | <20 |
| POPE | 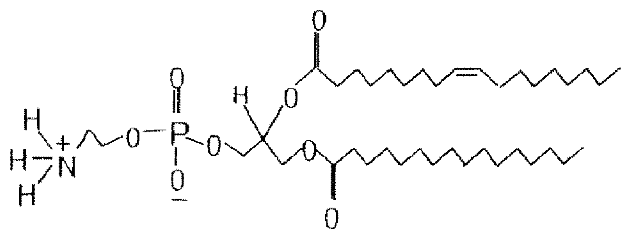 | Lamellar | <20 |
| DOPE | 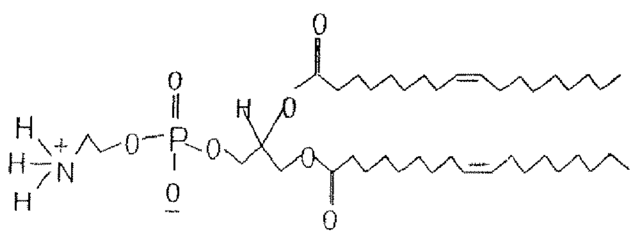 | Hexagonal$_{II}$ | 170 |

Figure 5

Peptide sequences used in the generation of peptide-liposome conjugates

1st generation conjugates

GTH1-2F5:        YKRWIILGLNKIVRMYS-QQEKNEQELLELDKWASLWN
GTH1-4E10:       YKRWIILGLNKIVRMYS-SLWNWFNITNWLWYIK
GTH1-V3 (Control): YKRWIILGLNKIVRMYS-KQIINMWQEVGKAMYACTRPNYNKRK
RIHIGPGRAFYTTK

2nd generation conjugates (native orientation)

MPER652-GTH1:
QQEKNEQELLELDKWASLWNWFNITNWLW-YIKYKRWIILGLNKIVRMYS

MPER656-GTH1:
NEQELLELDKWASLWNWFNITNWLW-YIKYKRWIILGLNKIVRMYS

MPER652 Scr.-GTH1:
EAWLWDLLIWNLQFEWKNNWTEQNQLEKS-YIKYKRWIILGLNKIVRMYS

Figure 6A

Additional 2nd Generation Peptides for Incorporation Into Liposomes

- 1). 4E10-GGG-GTH1:
- SLWNWFNITNWLWYIK-GGG-YKRWIILGLNKIVRMYS

- 2). Scr.4E10-GGG-GTH1:
- KNIWLSNYFWLINWWT-GGG-YKRWIILGLNKIVRMYS
- 3). 2F5-GGG-GTH1:
- QQEKNEQELLELDKWASLWN-GGG-YKRWIILGLNKIVRMYS
- 4). Scr.2F5-GGG-GTH1:
- NKEQDQAEESLQLWEKLNWL-GGG-YKRWIILGLNKIVRMYS
- 5). 4E10-GTH1:
- SLWNWFNITNWLWYIK-YKRWIILGLNKIVRMYS
- 6). Scr.4E10-GTH1:
- KNIWLSNYFWLINWWT-YKRWIILGLNKIVRMYS
- 7). 2F5-GTH1:
- QQEKNEQELLELDKWASLWN-YKRWIILGLNKIVRMYS
- 8). Scr.2F5-GTH1:
- NKEQDQAEESLQLWEKLNWL-YKRWIILGLNKIVRMYS

Schematic presentation of various designs of MPER gp41 constructs

Figure 9  Binding of 2F5 mAb to peptide-liposomes

Figure 10 A32 mAb (control) binding to peptide-liposomes

Figure 11 Generation of Fluorescein conjugated peptide-liposomes

Figure 12 Reactivity of immunized guinea pig sera with 4E10 peptide

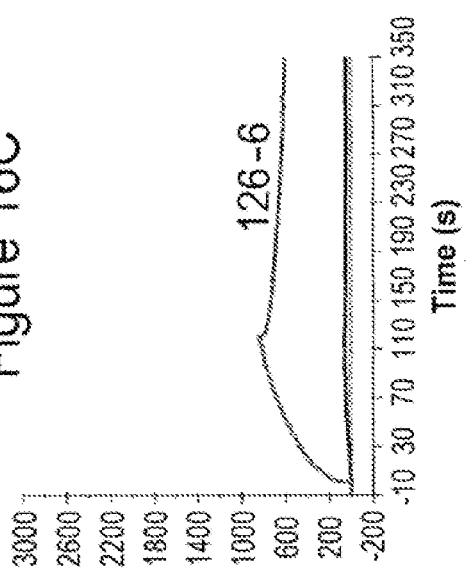
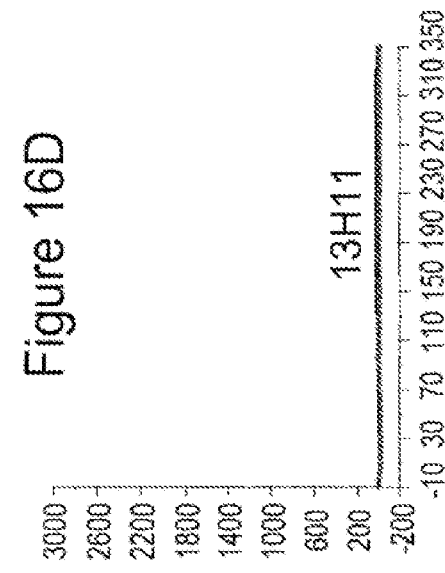
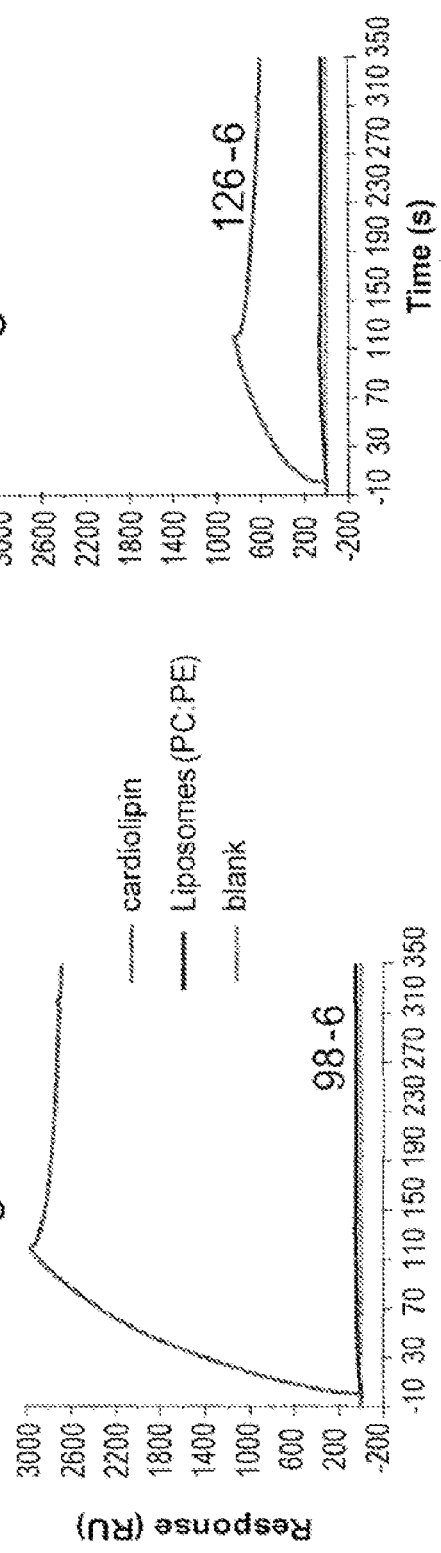
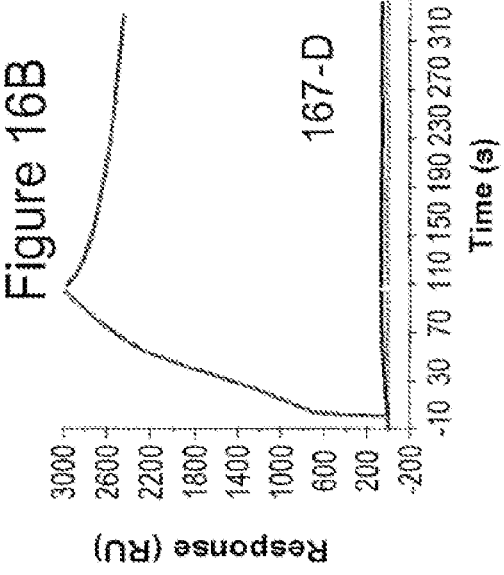
Figures 16 A-D

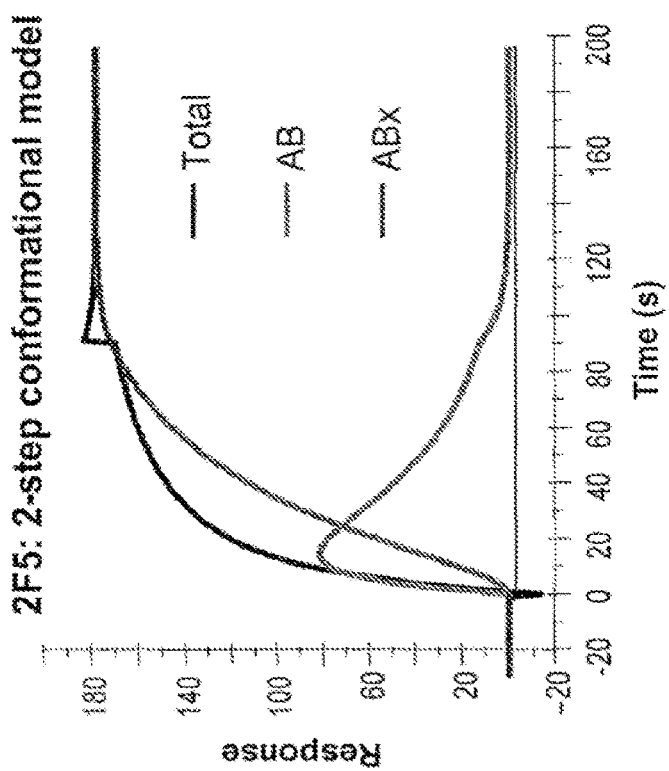
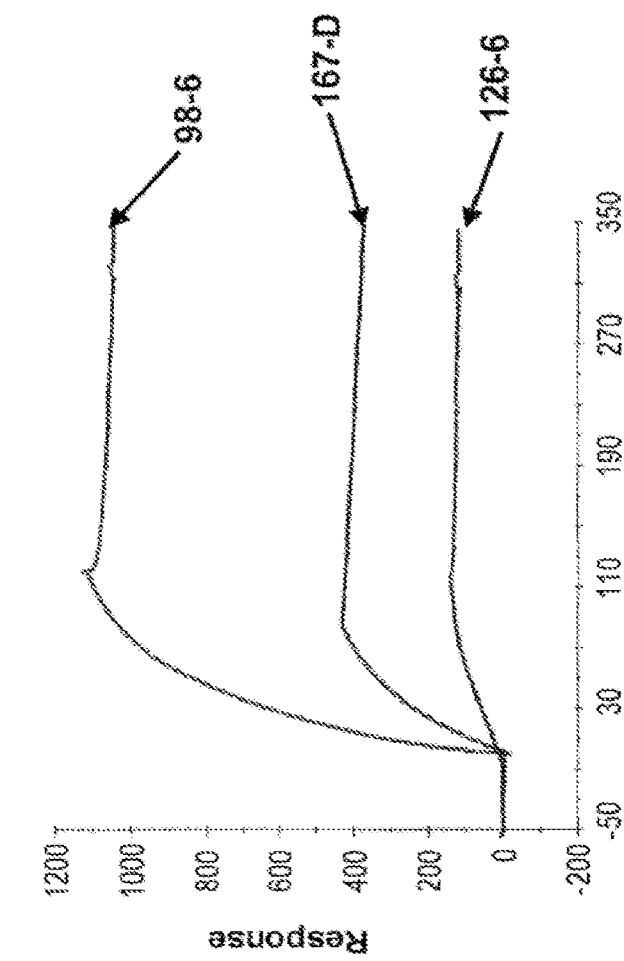
Figures 17 A-B

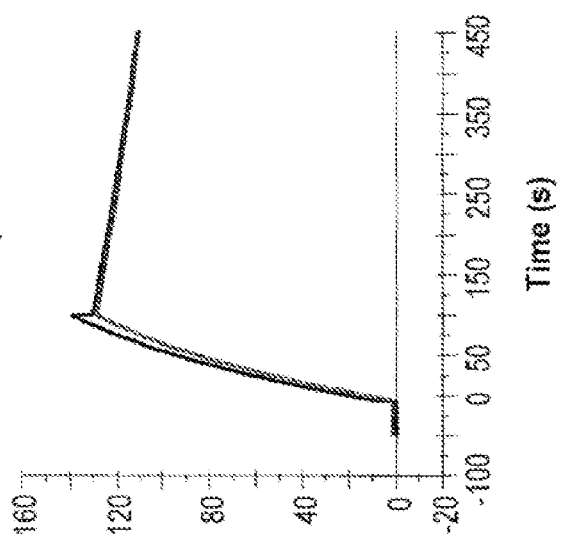
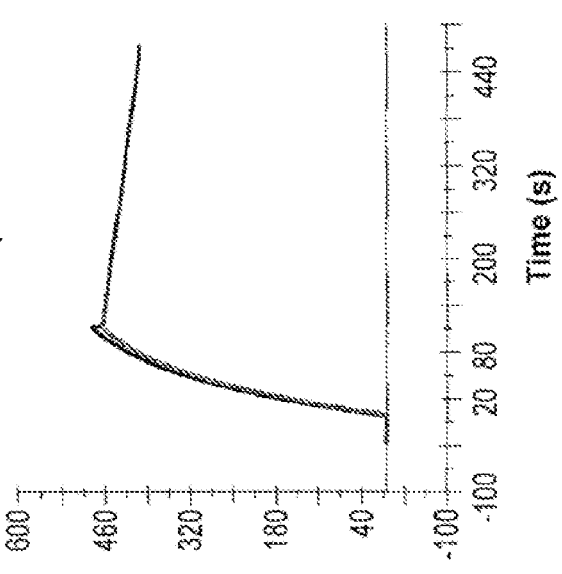
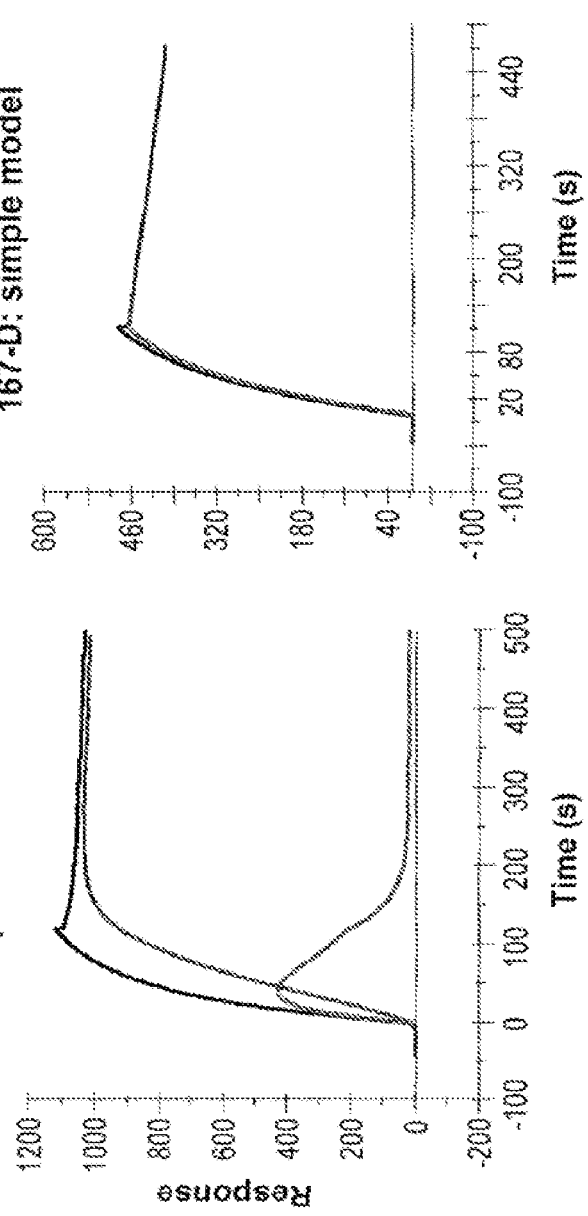
Figures 17 C-E

SEQUENCE LISTING

```
<160> NUMBER OF SEQ ID NOS: 28

<210> SEQ ID NO 1
<211> LENGTH: 32
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 1

Gln Gln Glu Lys Asn Glu Gln Glu Leu Leu Glu Leu Asp Lys Trp Ala
1               5                   10                  15

Ser Leu Trp Asn Trp Phe Asp Ile Thr Asn Trp Leu Trp Tyr Ile Lys
            20                  25                  30

<210> SEQ ID NO 2
<211> LENGTH: 57
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 2

Tyr Lys Arg Trp Ile Ile Leu Gly Leu Asn Lys Ile Val Arg Met Tyr
1               5                   10                  15

Ser Lys Gln Ile Ile Asn Met Trp Gln Glu Val Gly Lys Ala Met Tyr
            20                  25                  30
```

```
Ala Cys Thr Arg Pro Asn Tyr Asn Lys Arg Lys Arg Ile His Ile Gly
            35                  40                  45

Pro Gly Arg Ala Phe Tyr Thr Thr Lys
    50                  55

<210> SEQ ID NO 3
<211> LENGTH: 49
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 3

Gln Gln Glu Lys Asn Glu Gln Glu Leu Leu Glu Leu Asp Lys Trp Ala
1               5                   10                  15

Ser Leu Trp Asn Trp Phe Asn Ile Thr Asn Trp Leu Trp Tyr Ile Lys
            20                  25                  30

Tyr Lys Arg Trp Ile Ile Leu Gly Leu Asn Lys Ile Val Arg Met Tyr
            35                  40                  45

Ser

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 4

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys Tyr Lys Arg Trp
            20                  25                  30

Ile Ile Leu Gly Leu Asn Lys Ile Val Arg Met Tyr Ser
            35                  40                  45

<210> SEQ ID NO 5
<211> LENGTH: 49
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 5

Glu Ala Trp Leu Trp Asp Leu Leu Ile Trp Asn Leu Gln Phe Glu Trp
1               5                   10                  15

Lys Asn Asn Trp Thr Glu Gln Asn Gln Leu Glu Lys Ser Tyr Ile Lys
            20                  25                  30

Tyr Lys Arg Trp Ile Ile Leu Gly Leu Asn Lys Ile Val Arg Met Tyr
            35                  40                  45

Ser

<210> SEQ ID NO 6
<211> LENGTH: 36
<212> TYPE: PRT
<213> ORGANISM: Artificial Sequence
<220> FEATURE:
<223> OTHER INFORMATION: Description of Artificial Sequence: Synthetic
      HIV sequence
```

```
<400> SEQUENCE: 6

Ser Leu Trp Asn Trp Phe Asn Ile Thr Asn Trp Leu Trp Tyr Ile Lys
1               5                   10                  15

Gly Gly Gly Tyr Lys Arg Trp Ile Ile Leu Gly Leu Asn Lys Ile Val
            20                  25                  30

Arg Met Tyr Ser
        35

<210> SEQ ID NO 7
<211> LENGTH: 36
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 7

Lys Asn Ile Trp Leu Ser Asn Tyr Phe Trp Leu Ile Asn Trp Trp Thr
1               5                   10                  15

Gly Gly Gly Tyr Lys Arg Trp Ile Ile Leu Gly Leu Asn Lys Ile Val
            20                  25                  30

Arg Met Tyr Ser
        35

<210> SEQ ID NO 8
<211> LENGTH: 40
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 8

Gln Gln Glu Lys Asn Glu Gln Glu Leu Leu Glu Leu Asp Lys Trp Ala
1               5                   10                  15

Ser Leu Trp Asn Gly Gly Gly Tyr Lys Arg Trp Ile Ile Leu Gly Leu
            20                  25                  30

Asn Lys Ile Val Arg Met Tyr Ser
        35                  40

<210> SEQ ID NO 9
<211> LENGTH: 40
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 9

Asn Lys Glu Gln Asp Gln Ala Glu Glu Ser Leu Gln Leu Trp Glu Lys
1               5                   10                  15

Leu Asn Trp Leu Gly Gly Gly Tyr Lys Arg Trp Ile Ile Leu Gly Leu
            20                  25                  30

Asn Lys Ile Val Arg Met Tyr Ser
        35                  40

<210> SEQ ID NO 10
<211> LENGTH: 33
<212> TYPE: PRT
<213> ORGANISM: Artificial Sequence
<220> FEATURE:
<223> OTHER INFORMATION: Description of Artificial Sequence: Synthetic
      HIV sequence
```

<400> SEQUENCE: 10

Ser Leu Trp Asn Trp Phe Asn Ile Thr Asn Trp Leu Trp Tyr Ile Lys
1               5                   10                  15

Tyr Lys Arg Trp Ile Ile Leu Gly Leu Asn Lys Ile Val Arg Met Tyr
            20                  25                  30

Ser

<210> SEQ ID NO 11
<211> LENGTH: 33
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 11

Lys Asn Ile Trp Leu Ser Asn Tyr Phe Trp Leu Ile Asn Trp Trp Thr
1               5                   10                  15

Tyr Lys Arg Trp Ile Ile Leu Gly Leu Asn Lys Ile Val Arg Met Tyr
            20                  25                  30

Ser

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 12

Glu Leu Asp Lys Trp Ala Ser
1               5

<210> SEQ ID NO 13
<211> LENGTH: 37
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 13

Gln Gln Glu Lys Asn Glu Gln Glu Leu Leu Glu Leu Asp Lys Trp Ala
1               5                   10                  15

Ser Leu Trp Asn Tyr Lys Arg Trp Ile Ile Leu Gly Leu Asn Lys Ile
            20                  25                  30

Val Arg Met Tyr Ser
        35

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 14

Asn Lys Glu Gln Asp Gln Ala Glu Glu Ser Leu Gln Leu Trp Glu Lys
1               5                   10                  15

Leu Asn Trp Leu Tyr Lys Arg Trp Ile Ile Leu Gly Leu Asn Lys Ile

```
                    20                  25                  30

Val Arg Met Tyr Ser
            35

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 15

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Leu Gly
                20                  25                  30

Ile Trp Gly Cys Ser Gly Lys Leu Ile Cys Thr Thr Ala Val Pro Trp
            35                  40                  45

Asn Ala Ser Trp Ser Asn Lys Ser Leu Glu Tyr Thr Ser Leu Ile His
        50                  55                  60

Ser Leu Ile Glu Glu Ser Gln Asn Gln Gln Lys Asn Glu Gln Glu
65                  70                  75                  80

Leu Leu Glu Leu Asp Lys Trp Ala Ser Leu Trp Asn Trp Phe Tyr Lys
                85                  90                  95

Arg Trp Ile Ile Leu Gly Leu Asn Lys Ile Val Arg Met Tyr Ser His
            100                 105                 110

His His His His His
        115

<210> SEQ ID NO 16
<211> LENGTH: 89
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 16

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Tyr Thr
                20                  25                  30

Ser Leu Ile His Ser Leu Ile Glu Glu Ser Gln Asn Gln Gln Glu Lys
            35                  40                  45

Asn Glu Gln Glu Leu Leu Glu Leu Asp Lys Trp Ala Ser Leu Trp Asn
        50                  55                  60

Trp Phe Tyr Lys Arg Trp Ile Ile Leu Gly Leu Asn Lys Ile Val Arg
65                  70                  75                  80

Met Tyr Ser His His His His His His
                85

<210> SEQ ID NO 17
<211> LENGTH: 117
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 17
```

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Tyr Lys
                20                  25                  30

Arg Trp Ile Ile Leu Gly Leu Asn Lys Ile Val Arg Met Tyr Ser Leu
            35                  40                  45

Gly Ile Trp Gly Cys Ser Gly Lys Leu Ile Cys Thr Thr Ala Val Pro
        50                  55                  60

Trp Asn Ala Ser Trp Ser Asn Lys Ser Leu Glu Tyr Thr Ser Leu Ile
65                  70                  75                  80

His Ser Leu Ile Glu Glu Ser Gln Asn Gln Glu Lys Asn Glu Gln
                85                  90                  95

Glu Leu Leu Glu Leu Asp Lys Trp Ala Ser Leu Trp Asn Trp Phe His
                100                 105                 110

His His His His His
        115

<210> SEQ ID NO 18
<211> LENGTH: 89
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 18

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Tyr Lys
                20                  25                  30

Arg Trp Ile Ile Leu Gly Leu Asn Lys Ile Val Arg Met Tyr Ser Tyr
            35                  40                  45

Thr Ser Leu Ile His Ser Leu Ile Glu Glu Ser Gln Asn Gln Gln Glu
        50                  55                  60

Lys Asn Glu Gln Glu Leu Leu Glu Leu Asp Lys Trp Ala Ser Leu Trp
65                  70                  75                  80

Asn Trp Phe His His His His His His
                85

<210> SEQ ID NO 19
<211> LENGTH: 132
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 19

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Leu Gly
                20                  25                  30

Ile Trp Gly Cys Ser Gly Lys Leu Ile Cys Thr Thr Ala Val Pro Trp
        35                  40                  45

Asn Ala Ser Trp Ser Asn Lys Ser Leu Glu Tyr Thr Ser Leu Ile His
    50                  55                  60

Ser Leu Ile Glu Glu Ser Gln Asn Gln Gln Glu Lys Asn Glu Gln Glu
65                  70                  75                  80

```
Leu Leu Glu Leu Asp Lys Trp Ala Ser Leu Trp Asn Trp Phe Asn Ile
                85                  90                  95

Thr Asn Trp Leu Trp Tyr Ile Lys Leu Phe Ile Met Ile Val Gly Gly
            100                 105                 110

Leu Val Gly Leu Arg Ile Val Phe Ala Val Leu Ser Val His His
        115                 120                 125

His His His His
    130

<210> SEQ ID NO 20
<211> LENGTH: 104
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 20

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Tyr Thr
            20                  25                  30

Ser Leu Ile His Ser Leu Ile Glu Glu Ser Gln Asn Gln Gln Glu Lys
        35                  40                  45

Asn Glu Gln Glu Leu Leu Glu Leu Asp Lys Trp Ala Ser Leu Trp Asn
    50                  55                  60

Trp Phe Asn Ile Thr Asn Trp Leu Trp Tyr Ile Lys Leu Phe Ile Met
65                  70                  75                  80

Ile Val Gly Gly Leu Val Gly Leu Arg Ile Val Phe Ala Val Leu Ser
                85                  90                  95

Val Val His His His His His His
            100

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 21

Trp Phe Asn Ile Thr Asn Trp
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 22

Asn Trp Phe Asp Ile Thr
1               5

<210> SEQ ID NO 23
<211> LENGTH: 6
<212> TYPE: PRT
<213> ORGANISM: Artificial Sequence
<220> FEATURE:
```

<223> OTHER INFORMATION: Description of Artificial Sequence: Synthetic
      HIV sequence

<400> SEQUENCE: 23

Glu Leu Asp Lys Trp Ala
1               5

<210> SEQ ID NO 24
<211> LENGTH: 852
<212> TYPE: PRT
<213> ORGANISM: Artificial Sequence
<220> FEATURE:
<223> OTHER INFORMATION: Description of Artificial Sequence: Synthetic
      HIV consensus sequence

<400> SEQUENCE: 24

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
                20                  25                  30

Leu Trp Val Thr Val Tyr Tyr Gly Val Pro Val Trp Lys Glu Ala Asn
            35                  40                  45

Thr Thr Leu Phe Cys Ala Ser Asp Ala Lys Ala Tyr Asp Thr Glu Val
50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asn Val Asn Val Thr Asn Thr Thr Asn Asn Thr Glu Glu
130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
                180                 185                 190

Cys Asn Thr Ser Ala Ile Thr Gln Ala Cys Pro Lys Val Ser Phe Glu
            195                 200                 205

Pro Ile Pro Ile His Tyr Cys Ala Pro Ala Gly Phe Ala Ile Leu Lys
210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
                260                 265                 270

Asn Ile Thr Asn Asn Ala Lys Thr Ile Ile Val Gln Leu Asn Glu Ser
            275                 280                 285

Val Glu Ile Asn Cys Thr Arg Pro Asn Asn Asn Thr Arg Lys Ser Ile
290                 295                 300

Arg Ile Gly Pro Gly Gln Ala Phe Tyr Ala Thr Gly Asp Ile Ile Gly
305                 310                 315                 320

-continued

```
Asp Ile Arg Gln Ala His Cys Asn Ile Ser Gly Thr Lys Trp Asn Lys
            325                 330                 335

Thr Leu Gln Gln Val Ala Lys Lys Leu Arg Glu His Phe Asn Asn Lys
        340                 345                 350

Thr Ile Ile Phe Lys Pro Ser Ser Gly Gly Asp Leu Glu Ile Thr Thr
    355                 360                 365

His Ser Phe Asn Cys Arg Gly Glu Phe Phe Tyr Cys Asn Thr Ser Gly
370                 375                 380

Leu Phe Asn Ser Thr Trp Ile Gly Asn Gly Thr Lys Asn Asn Asn Asn
385                 390                 395                 400

Thr Asn Asp Thr Ile Thr Leu Pro Cys Arg Ile Lys Gln Ile Ile Asn
            405                 410                 415

Met Trp Gln Gly Val Gly Gln Ala Met Tyr Ala Pro Pro Ile Glu Gly
        420                 425                 430

Lys Ile Thr Cys Lys Ser Asn Ile Thr Gly Leu Leu Leu Thr Arg Asp
    435                 440                 445

Gly Gly Asn Asn Asn Thr Asn Glu Thr Glu Ile Phe Arg Pro Gly Gly
450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
            485                 490                 495

Val Val Glu Arg Glu Lys Arg Ala Val Gly Ile Gly Ala Val Phe Leu
        500                 505                 510

Gly Phe Leu Gly Ala Ala Gly Ser Thr Met Gly Ala Ala Ser Ile Thr
    515                 520                 525

Leu Thr Val Gln Ala Arg Gln Leu Leu Ser Gly Ile Val Gln Gln Gln
530                 535                 540

Ser Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
            565                 570                 575

Arg Tyr Leu Lys Asp Gln Gln Leu Leu Gly Ile Trp Gly Cys Ser Gly
        580                 585                 590

Lys Leu Ile Cys Thr Thr Thr Val Pro Trp Asn Ser Ser Trp Ser Asn
    595                 600                 605

Lys Ser Gln Asp Glu Ile Trp Asp Asn Met Thr Trp Met Glu Trp Glu
        610                 615                 620

Arg Glu Ile Asn Asn Tyr Thr Asp Ile Ile Tyr Ser Leu Ile Glu Glu
625                 630                 635                 640

Ser Gln Asn Gln Gln Glu Lys Asn Glu Gln Glu Leu Leu Ala Leu Asp
            645                 650                 655

Lys Trp Ala Ser Leu Trp Asn Trp Phe Asp Ile Thr Asn Trp Leu Trp
        660                 665                 670

Tyr Ile Lys Ile Phe Ile Met Ile Val Gly Gly Leu Ile Gly Leu Arg
    675                 680                 685

Ile Val Phe Ala Val Leu Ser Ile Val Asn Arg Val Arg Gln Gly Tyr
690                 695                 700

Ser Pro Leu Ser Phe Gln Thr Leu Ile Pro Asn Pro Arg Gly Pro Asp
705                 710                 715                 720

Arg Pro Glu Gly Ile Glu Glu Gly Gly Glu Gln Asp Arg Asp Arg
            725                 730                 735

Ser Ile Arg Leu Val Asn Gly Phe Leu Ala Leu Ala Trp Asp Asp Leu
```

```
              740                 745                 750
Arg Ser Leu Cys Leu Phe Ser Tyr His Arg Leu Arg Asp Phe Ile Leu
            755                 760                 765

Ile Ala Ala Arg Thr Val Glu Leu Leu Gly Arg Lys Gly Leu Arg Arg
770                 775                 780

Gly Trp Glu Ala Leu Lys Tyr Leu Trp Asn Leu Leu Gln Tyr Trp Gly
785                 790                 795                 800

Gln Glu Leu Lys Asn Ser Ala Ile Ser Leu Leu Asp Thr Thr Ala Ile
                805                 810                 815

Ala Val Ala Glu Gly Thr Asp Arg Val Ile Glu Val Val Gln Arg Ala
            820                 825                 830

Cys Arg Ala Ile Leu Asn Ile Pro Arg Arg Ile Arg Gln Gly Leu Glu
        835                 840                 845

Arg Ala Leu Leu
    850

<210> SEQ ID NO 25
<211> LENGTH: 2559
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
atgcgcgtgc gcggcatcca gcgcaactgc cagcacctgt ggcgctgggg cacccctgatc      60 ctgggcatgc tgatgatctg ctccgccgcc gagaacctgt gggtgaccgt gtactacggc     120
gtgcccgtgt ggaaggaggc caacaccacc ctgttctgcg cctccgacgc caaggcctac     180
gacaccgagt gcacaacgt gtgggccacc cacgcctgcg tgcccaccga ccccaacccc      240
caggagatcg tgctggagaa cgtgaccgag aacttcaaca tgtggaagaa caacatggtg     300
gagcagatgc acgaggacat catctccctg tgggaccagt ccctgaagcc ctgcgtgaag     360 ctgaccccc tgtgcgtgac cctgaactgc accaacgtga acgtgaccaa caccaccaac      420
aacaccgagg agaagggcga gatcaagaac tgctccttca acatcaccac cgagatccgc     480
gacaagaagc agaaggtgta cgccctgttc taccgcctgg acgtggtgcc catcgacgac     540
aacaacaaca actcctccaa ctaccgcctg atcaactgca cacctccgc catcacccag       600 gcctgcccca aggtgtcctt cgagcccatc cccatccact actgcgcccc cgccggcttc     660
gccatcctga gtgcaacga caagaagttc aacggcaccg cccctgcaa gaacgtgtcc       720 accgtgcagt gcacccacgg catcaagccc gtggtgtcca cccagctgct gctgaacggc     780
tccctggccg aggaggagat catcatccgc tccgagaaca tcaccaacaa cgccaagacc     840
atcatcgtgc agctgaacga gtccgtggag atcaactgca cccgccccaa caacaacacc    900
cgcaagtcca tccgcatcgg ccccggccag gccttctacg ccaccggcga catcatcggc     960
gacatccgcc aggcccactg caacatctcc ggcaccaagt ggaacaagac cctgcagcag    1020
gtggccaaga agctgcgcga gcacttcaac aacaagacca tcatcttcaa gccctcctcc    1080
ggcggcgacc tggagatcac cacccactcc ttcaactgcc gcggcgagtt cttctactgc    1140
aacacctccg gcctgttcaa ctccacctgg atcggcaacg caccaagaa caacaacaac    1200 accaacgaca ccatcacccct gcctgccgc atcaagcaga tcatcaacat gtggcagggc    1260
gtgggccagg ccatgtacgc ccccccatc gagggcaaga tcacctgcaa gtccaacatc    1320
accggcctgc tgctgacccg cgacggcggc aacaacaaca ccaacgagac cgagatcttc    1380
```

```
cgccccggcg gcggcgacat gcgcgacaac tggcgctccg agctgtacaa gtacaaggtg    1440
gtgaagatcg agccctggg cgtggcccc accaaggcca agcgccgcgt ggtggagcgc     1500
gagaagcgcg ccgtgggcat cggcgccgtg ttcctgggct tcctgggcgc cgccggctcc    1560
accatgggcg ccgcctccat caccctgacc gtgcaggccc gccagctgct gtccggcatc    1620
gtgcagcagc agtccaacct gctgcgcgcc atcgaggccc agcagcacct gctgcagctg    1680
accgtgtggg gcatcaagca gctgcaggcc cgcgtgctgg ccgtggagcg ctacctgaag    1740
gaccagcagc tgctgggcat ctggggctgc tccggcaagc tgatctgcac caccaccgtg    1800
ccctggaact cctcctggtc caacaagtcc caggacgaga tctgggacaa catgacctgg    1860
atggagtggg agcgcgagat caacaactac accgacatca tctactccct gatcgaggag    1920
tcccagaacc agcaggagaa gaacgagcag gagctgctgg ccctggacaa gtgggcctcc    1980
ctgtggaact ggttcgacat caccaactgg ctgtggtaca tcaagatctt catcatgatc    2040
gtgggcggct gatcggcct gcgcatcgtg ttcgccgtgc tgtccatcgt gaaccgcgtg    2100
cgccagggct actcccccct gtccttccag accctgatcc ccaaccccg cggccccgac    2160 cgccccgagg gcatcgagga ggagggcggc gagcaggacc gcgaccgctc catccgcctg    2220
gtgaacggct tcctggccct ggcctgggac gacctgcgct ccctgtgcct gttctcctac    2280
caccgcctgc gcgacttcat cctgatcgcc gcccgcaccg tggagctgct gggccgcaag    2340
ggcctgcgcc gcggctggga ggccctgaag tacctgtgga acctgctgca gtactggggc    2400
caggagctga gaactccgc catctccctg ctggacacca ccgccatcgc cgtggccgag    2460
ggcaccgacc gcgtgatcga ggtggtgcag cgcgcctgcc gcgccatcct gaacatcccc    2520
cgccgcatcc gccagggcct ggagcgcgcc ctgctgtaa                          2559
```

```
<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 26

Tyr Lys Arg Trp Ile Ile Leu Gly Leu Asn Lys Ile Val Arg Met Tyr
1               5                   10                  15

Ser Gln Gln Glu Lys Asn Glu Gln Glu Leu Leu Glu Leu Asp Lys Trp
            20                  25                  30

Ala Ser Leu Trp Asn
        35

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 27

Tyr Lys Arg Trp Ile Ile Leu Gly Leu Asn Lys Ile Val Arg Met Tyr
1               5                   10                  15

Ser Ser Leu Trp Asn Trp Phe Asn Ile Thr Asn Trp Leu Trp Tyr Ile
            20                  25                  30

Lys
```

-continued

```
<210> SEQ ID NO 28
<211> LENGTH: 32
<212> TYPE: PRT
<213> ORGANISM: Artificial Sequence
<220> FEATURE:
<223> OTHER INFORMATION: Description of Artificial Sequence: Synthetic
      HIV sequence

<400> SEQUENCE: 28

Lys Trp Ala Ser Leu Trp Asn Trp Phe Asp Ile Thr Asn Trp Leu Tyr
1               5                   10                  15

Lys Arg Trp Ile Ile Leu Gly Leu Asn Lys Ile Val Arg Met Tyr Ser
            20                  25                  30
```

LIPOSOME-PEPTIDE CONJUGATE AND METHOD OF USING SAME TO INDUCE PRODUCTION OF ANTI-HIV ANTIBODIES

This application is a continuation of U.S. application Ser. No. 15/195,841, filed Jun. 28, 2016, which is a divisional of U.S. application Ser. No. 11/785,077, filed Apr. 13, 2007 and issued as U.S. Pat. No. 9,402,893, which is a continuation-in-part of International Application No. PCT/US2006/013684, filed Apr. 12, 2006, which claims priority from U.S. Provisional Application No. 60/670,243, filed Apr. 12, 2005, U.S. Provisional Application No. 60/675,091, filed Apr. 27, 2005, U.S. Provisional Application No. 60/697,997, filed Jul. 12, 2005, and U.S. Provisional Application No. 60/757,478, filed Jan. 10, 2006, the entire contents of each are incorporated herein by reference.

SEQUENCE LISTING

The instant application contains a Sequence Listing which has been filed electronically in ASCII format and is hereby incorporated by reference in its entirety. Said ASCII copy, created on Jan. 22, 2018, is named 1234300_277US1_SL.txt and is 26,596 bytes in size.

TECHNICAL FIELD

The present invention relates, in general, to human immunodeficiency virus (HIV), and, in particular, to a method of inducing neutralizing antibodies to HIV and to compounds and compositions suitable for use in such a method.

BACKGROUND

The first antibodies that are made in acute HIV-1 infection are against the CD4 binding site (Moore et al, J. Virol. 68(8) 5142 (1994)), the CCR5 co-receptor binding site (Choe et al, Cell 1 14(2):161-170 (2003)), and the V3 loop (Moore et al, J. Acquir. Immun. Def. Syn. 7(4):332 (1994)). However, these antibodies do not control HIV-1 and are easily escaped (Burton et al, Nature Immun. 5:233-236 (2004), Wei et al, Nature 422(6929):307-312 (2003)). Neutralizing antibodies against autologous virus develop fifty to sixty days after infection, but antibodies capable of neutralizing heterologous HIV-1 strains do not arise until after the first year of infection (Richman et al, Proc. Natl. Acad. Sci. USA 100 (7):4144-4149 (2003), Wei et al, Nature 422(6929):307-312 (2003)).

The four epitopes on HIV-1 envelope to which rare broadly reactive neutralizing antibodies bind are the CD4 binding site (CD4BS) (mab (monoclonal antibody) IgG1b12) (Zwick et al, J. Virol. 77(10):5863-5876 (2003)), the membrane proximal external region (MPER) epitopes defined by human mabs 2F5 and 4E10 (Armbruster et al, J. Antimicrob. Chemother. 54:915-920 (2004), Stiegler and Katinger, J. Antimicrob. Chemother. 51:757-759 (2003), Zwick et al, Journal of Virology 79:1252-1261 (2005), Purtscher et al, AIDS 10:587 (1996)) (FIG. 1), and the mannan glycan epitope defined by human mab 2G12 (Scanlan et al, Adv. Exper. Med. Biol. 535:205-218 (2003)). These four rare human mabs are all unusual: two are IgG3 (2F5 and 4E10), one has a unique Ig dimer structure (2G12), one has a very hydrophobic CDR3 (2F5) (Ofek et al, J. Virol. 198:10724 (2004)), and, in all four, the CDR3 is unusually long (Burton et al, Nature Immunol. 5(3):233-236 (2004), Kunert et al, AIDS Res. Hum. Retroviruses 20(7):755-762 (2004), Zwick et al, J. Virol. 78(6):3155-3161 (2004), Cardoso et al, Immunity 22:163-172 (2005)). Of these, 2F5- and 4E10-like human mabs are quite rare. Acute HIV-1 patients do not make antibodies against the MPER or 2G12 epitopes (Robinson, unpublished (2005), Shaw, unpublished (2005), MPER can be defined as amino acids 652 to 683 of HIV envelope (Cardoso et al, Immunity 22:163-173 (2005) (e.g., QQEKNEQELLELDKWASLWNWFDITNWLWYIK) (SEQ ID NO:1). CD4 binding site (BS) antibodies are commonly made early in HIV-1 infection, but these antibodies generally do not have the broad spectrum of neutralization shown by mab IgG1b12 (Burton et al, Nat. Immunol. 5(3):233-236 (2004)).

A number of epitopes of the HIV-1 envelope have been shown to cross-react with host tissues (Pinto et al, AIDS Res. Hum. Retrov. 10:823-828 (1994), Douvas et al, AIDS Res. Hum. Retrov. 10:253-262 (1994), Douvas et al, AIDS Res. Hum. Retrov. 12:1509-1517 (1996)), and autoimmune patients have been shown to make antibodies that cross-react with HIV proteins (Pinto et al, AIDS Res. Hum. Retrov. 10:823-828 (1994), Douvas et al, AIDS Res. Hum. Retrov. 10:253-262 (1994), Douvas et al, AIDS Res. Hum. Retrov. 12:1509-1517 (1996), Barthel et al, Semin. Arthr. Rheum. 23:1-7 (1993)). Similarly, induction of immune responses to self-epitopes has been suggested to be a cause of the autoimmune abnormalities and T cell depletion in AIDS (Douvas et al, AIDS Res. Hunt Retrov. 12:1509-1517 (1996), Ziegler et al, Clin. Immunol. Immunopath. 41:305-313 (1986)).

High affinity peptide ligands for the 2F5 mab have been made that induce high levels of antibody against the peptide but do not broadly neutralize HIV-1 primary isolates (McGaughey et al, Biochemistry 42(11):3214-3223 (2003), Zhang et al, J. Virol. 78(15):8342-8348 (2004), rev. in Zwick et al, J. Virol. 79:1252-1261 (2005)). These results have been interpreted to mean that the peptide ligands for 2F5 are not in the appropriate conformation for induction of anti-MPER antibodies (Burton et al, Nature Immunology 5(3): 233-236 (2004), Zwick et al, J. Virol. 79:1252-1261 (2005)). A series of highly constrained HIV-1 Env immunogens have been made with the IgG1b12, 2G12, 2F5 and 4E10 epitopes stably expressed, and it has been demonstrated that these immunogens do not induce broadly reactive neutralizing antibodies in guinea pigs or rabbits, and, specifically, do not make neutralizing antibodies to the MPER epitopes (Liao et al, J. Virol. 78(10):5270-5278 (2004); Haynes, unpublished (2005)). These results have raised the question as to whether broadly reactive neutralizing antibodies to HIV-1 envelope are not made in normal animals and humans because they cannot be made.

Because long, hydrophobic CDR3 regions are typical of natural polyreactive autoantibodies (Meffre et al, J. Clin. Invest. 108:879-886 (2001), Ramsland et al, Exp. Clin. Immun. 18:176-198 (2001)), and HIV-1-infected patient B lymphocytes are polyclonally driven to make cardiolipin antibodies (Weiss et al, Clin. Immunol. Immunopathol. 77:69-74 (1995), Grunewald et al, Clin. Exp. Immunol. 15:464-71 (1999)), studies were undertaken to assay these and other anti-HIV-1 mabs for cardiolipin and other autoantigen reactivities. The present invention results, at least in part, from the realization that two broadly reactive HIV-1 envelope gp 41 human mabs, 2F5 and 4E10, are polyspecific autoantibodies reactive with cardiolipin.

SUMMARY OF THE INVENTION

The present invention relates generally to human HIV. More specifically, the invention relates to a method of inducing neutralizing antibodies to HIV and to compounds and compositions suitable for use in such a method. In a specific embodiment, the present invention provides immunogens that present MPER epitopes in their native membrane bound environment, and immunization methods using such immunogens that break tolerance.

Objects and advantages of the present invention will be clear from the description that follows.

BRIEF DESCRIPTION OF THE DRAWINGS

FIGS. 2A-2D. Reactivity of 2F5, 4E10, IgG1b12 Mabs with human Hep-2 epithelial cells. FIG. 2A shows Mab 2F5 reacting with Hep-2 cells in a diffuse cytoplasmic and nuclear pattern, FIG. 2B shows Mab 4E10 reacting with HEp-2 cells in a pattern similar to 2F5. FIG. 2C shows Mab IgG1b12 reacting with Rep-2 cells in a diffuse cytoplasmic pattern, with nucleoli reactive in the nucleus. FIG. 2C insert shows higher magnification of cells showing the nucleolar reactivity of IgG1b12 (arrows). FIG. 2D shows negative reactivity of Mab 1.9F on Hep-2 cells. Antibody amounts per slide assayed in FIGS. 2A-2D were 3.75 µg per slide of Mab. Mab 2F5 was positive on HEp-2 cells at 0.125 µg per slide (5 µg/ml). Mab 4E10 was positive on HEp-2 at 0.125 µg per slide (5 µg/ml), and IgG1b12 was positive at 1.25 µg per slide (50 µg/ml). All FIGS. X200.; FIG. 2C insert X400. Images shown are from an experiment representative of three performed.

FIG. 3A shows ELISA reactivity of MAbs 4E10 (solid bars) and 2F5 (open bars) to cardiolipin (CL), phosphatidylserine (PS), phosphatidylcholine (PC), phophatidylethanolamine (PE), and sphingomyelin (SM). Whereas both 4E10 and 2F5 reacted with cardiolipin, only 4E10 reacted with the other lipids tested. Reactivity of control human anti-CCR5 binding site MAb 1.7b was negative (data not shown). Reactivity of MAbs against empty coated plate was similarly negative (not shown). To show specificity of binding of MAb 2F5 to cardiolipin, 150-300 µg/ml of 2F5 and 1000 µg/ml of anti-2F5 idiotype murine MAb 3H6, which blocks the neutralization of HIV-1 by MAb 2F5 (Kunert et al, AIDS 16:667 (2002)), were used. The 2F5 anti-idiotype significantly blocked the binding of MAb 2F5 to cardiolipin by a mean of 70% in 3 separate experiments (p<0.03) (FIG. 3B). In a separate ELISA, MAb 2F5 bound to cardiolipin in half-maximal (EC50) response of 660 nM (not shown). FIG. 3C shows the dose response curve of 4E10 MAI) binding to cardiolipin. The half-maximal (EC50) response of 4E10 binding (80 nM) was calculated from a four parametric, sigmoidal curve fitting analysis. Binding data was acquired from an ELISA of 4E10 MAb binding (0.5 nM-1000 nM) to cardiolipin coated on ELISA plate (1.35 µg/well). FIG. 3D shows soluble HIV-1 Env gp140 oligomers (CON-S) expressing the 4E10 epitope inhibits binding of 4E10 MAb to cardiolipin. The IC50 of inhibition of 4E10 binding to cardiolipin was calculated to be 145 nM. The inhibition assay was carried out by using varying concentrations of gp140 (19.25-1230 nM) mixed with 10 µg/ml of 4E10 MAb, which were then added to wells containing 1.35 µg of cardiolipin. MAb 3H6 (1 mg/ml) (but not control MAb) also blocked the binding of MAb 2F5 to SSA/Ro, centromere B, and histones (not shown). All data in FIGS. 3A-3D are representative of at least two experiments performed.

FIGS. 4A and 4B. Amino acid (FIG. 4A) (SEQ ID NO:24) and nucleic acid (FIG. 4B) (SEQ ID NO:25) sequences of CON-S Env gp160. A CFI form of the protein of FIG. 4A was used in Example 2. (Gp14OCFI refers to an HIV-1 envelope design with the cleavage site (C), fusion site (F), and gp41 immunodominant region (I) deleted in addition to the deletion of the transmembrane and cytoplasmic domains.)

FIG. 5. Structures of phosphopholipids used in immunization regimens and resulting neutralization titers.

FIGS. 6A and 6B. Peptide sequences used in the generation of peptide-liposome conjugates (FIG. 6A (SEQ ID NOs:26, 27, 2, 3, 4, and 5); FIG. 6B (SEQ ID NOs:6, 7, 8, 9, 10, 11, 13, and 14). The nominal epitopes of mAbs 2F5 and 4E10 binding epitopes include sequences ELDKWAS (SEQ ID NO:12) and WFNITNW (SEQ ID NO:21), respectively, and are underlined. The V3 sequences were derived from gp120 of HIV-1 MN strain and were used as a control construct. Scrambled sequences are used controls.

FIGS. 16A-16D. Human Cluster II mAbs bound strongly to the anionic phospholipid, cardiolipin. Synthetic liposomes (PC:PE, green), or cardiolipin (red) was anchored on a BIAcore L1 sensor chip through hydrophobic interactions with the lipid linker. Each of the indicated mAb (500 nM) was injected over each of the lipid surface and a blank control surface. Strong binding of Cluster II mAb 98-6 and 167-D and moderate binding of mAb 126-6 is shown. No binding of the anti-MPER mAb 13H11 to either lipid was observed.

FIGS. 17A-17E. Human Cluster II mAb 98-6 bound to 2F5 peptide-lipid conjugates with higher avidity and followed the 2-step conformational change model. (A) 2F5-peptide (SP62) lipid conjugates were anchored to a BIAcore L1 surface and binding to mab 98-6, 167-D or 126-6 was monitored. Mab 98-6 bound strongly to the peptide-lipid conjugates, while relatively lower avidity binding was detected with mAb 167-D and 126-6. Curve fitting analysis show a 2-step conformational change associated binding of 2F5 (B) and 98-6 (C); while the binding of mAbs 167-D and 126-6 followed a simple model (Langmuir equation).

DETAILED DESCRIPTION OF THE INVENTION

Figure 1:
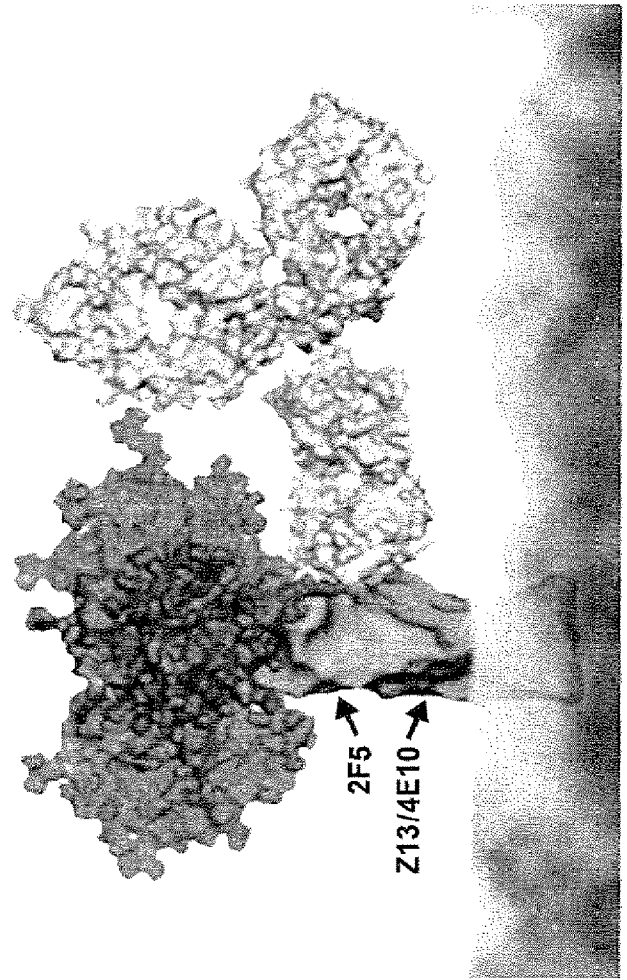
FIG. 1. Broadly neutralizing antibodies (2F5, 4E10) bind to epitopes that lie proximal to the host membrane. Both 2F5 (SEQ ID NO:12) and 4E1 (SEQ ID NO:21) mAbs are IgG3, have long CDR3s, and bind to epitopes that lie within HIV-1 gp41 (aa 660-683) membrane proximal external region (MPER).
Figure 3A:
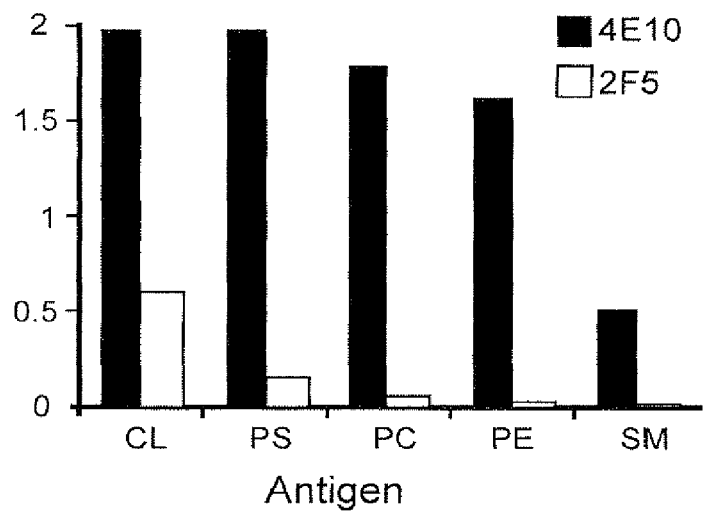
FIGS. 3A-3D. Assay of Mabs 2F5 and 4E10 against lipids and specificity of binding.
Figure 3B:
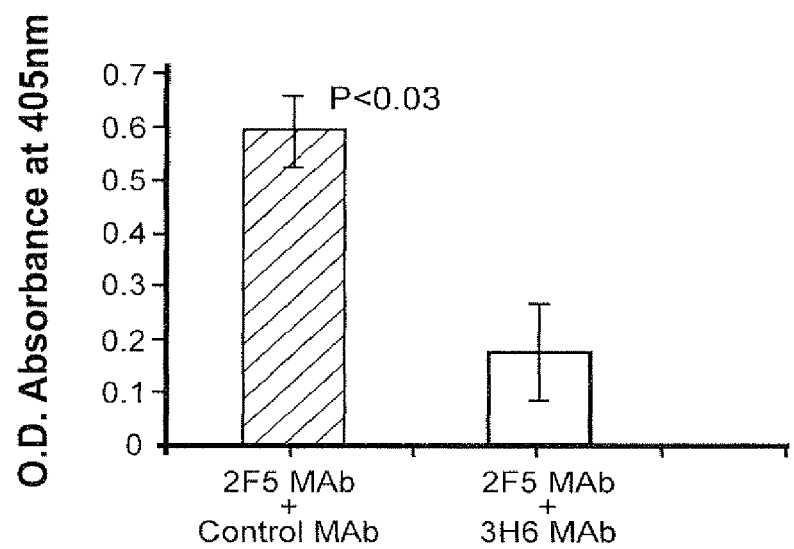
Figure 3C:
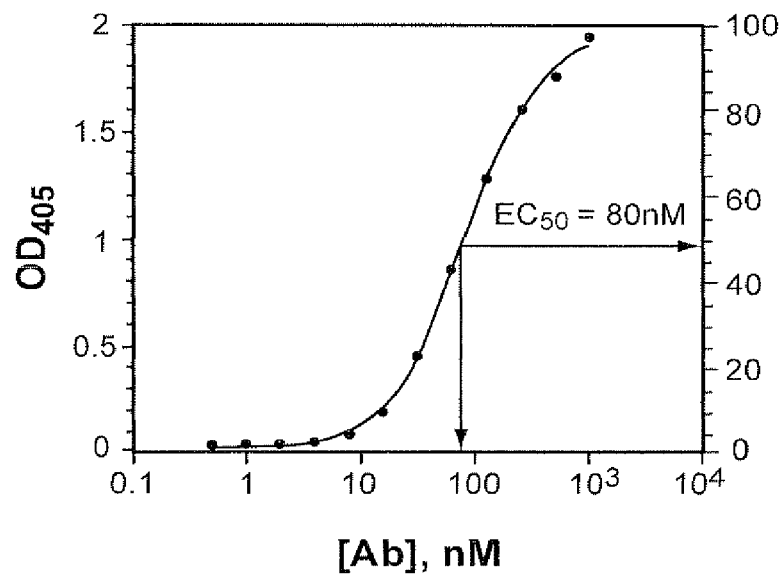
Figure 3D:
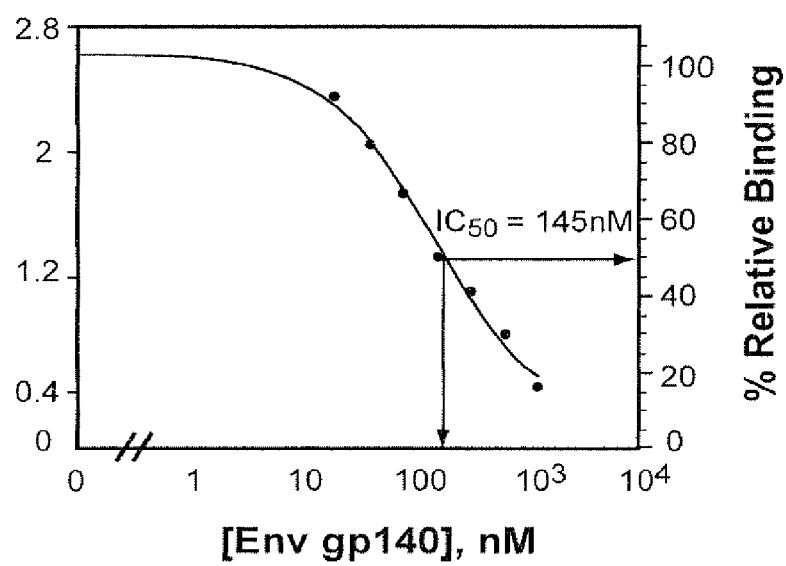

The present invention results, at least in part, from studies demonstrating that certain broadly neutralizing HIV-1 antibodies are autoantibodies. A large number of HIV+patients transiently make low levels of such antibodies, however, the studies described herein indicate that gp41 epitopes do not induce these antibody specificities but, rather, that cross-reactive autoantigens, including cardiolipin, are the priming antigen.

The present invention provides a method of inducing antibodies that neutralize HIV. The method comprises administering to a patient in need thereof an amount of at least one heterologous (e.g., non-human) or homologous (e.g., human) cross-reactive autoantigen sufficient to effect the induction. Cross-reactive autoantigens suitable for use in the instant invention include cardiolipin, SS-A/RO, dsDNA from bacteria or mammalian cells, centromere B protein and RiBo nucleoprotein (RNP).

Suitable autoantigens also include phospholipids in addition to cardiolipin, such as phosphatidylserine, phosphatidylethanolamine, phosphatidylcholine, phosphotidylinositol, sphingomyelin, and derivatives thereof, e.g., 1-palmitoyl-2-oleoyl-sn-glycero-3-[phospho-L-serine] (POPS), 1-palmitoyl-2-oleoyl-phosphatidylethanolamine (POPE), and dioleoyl phosphatidylethanolamine (DOPE). Use of hexagonal 11 phases of phospholipids can be advantageous and phospholipids that readily form hexagonally packed cylinders of the hexagonal 11 tubular phase (e.g., under physiological conditions) are preferred, as are phospholipids that can be stabilized in the hexagonal 11 phase. (See Rauch et al, Proc. Natl. Acad. Sci. USA 87:4112-4114 (1990); Aguilar et al et al, J. Biol. Chem. 274: 25193-25196 (1999)).

Fragments of such autoantigens comprising the cross-reactive epitopes can also be used.

The autoantigen, or fragment thereof, can be used, for example, in prime boost regimens that can be readily optimized by one skilled in the art (DNA sequences encoding proteinaceous components of such regimens can be administered under conditions such that the proteinaceous component is produced in vivo). By way of example, cross-reactive autoantigen can be used as a first vaccine prime to boost natural auto-antibodies (e.g., anti-cardiolipin 4E10- and 2F5-like antibodies). Either autoantigen (e.g., cardiolipin (or fragment thereof)), or an HIV-envelope protein/polypeptide/peptide comprising a cross-reactive epitope(s), such as the 2F5 and/or 4E10 epitopes (which epitopes can include at least the sequences ELDKWA (SEQ ID NO:23) and NWFDIT (SEQ ID NO:22), respectively), can be used as the boost. (See sequences disclosed in PCT/US04/30397.) (It will be appreciated that HIV-envelope is not an autoantigen.)

The mode of administration of the autoantigen and/or HIV-protein/polypeptide/peptide, or encoding sequence, can vary with the immunogen, the patient and the effect sought, similarly, the dose administered. Optimum dosage regimens can be readily determined by one skilled in the art. Typically, administration is subcutaneous, intramuscular, intravenous, intranasal or oral.

The immunogenic agents can be administered in combination with an adjuvant. While a variety of adjuvants can be used, preferred adjuvants include CpG oligonucleotides and other agents (e.g., TRL9 agonists) that can break tolerance to autoantigens without inducing autoimmune disease (Tran et al, Clin. Immunol. 109:278-287 (2003), US Appln Nos. 20030181406, 20040006242, 20040006032, 20040092472, 20040067905, 20040053880, 20040152649, 20040171086, 20040198680, 200500059619).

The invention includes compositions suitable for use in the instant method, including compositions comprising the autoantigen, and/or HIV protein/polypeptide/peptide comprising one or more cross-reactive epitopes (e.g., 4E10 and/or 2F5 epitopes), or 4E10 or 2F5 epitope mimics, and a carrier. When a DNA prime or boost can be used, suitable formulations include a DNA prime and a recombinant adenovirus boost and a DNA prime and a recombinant mycobacteria boost, where the DNA or the vectors encode, for example, either HIV envelope or a protein autoantigen, such as SS-A/Ro. Other combinations of these vectors can be used as primes or boosts, either with or without HIV protein/polypeptide/peptide and/or autoantigen. The composition can be present, for example, in a form suitable for injection or nasal administration. Advantageously, the composition is sterile. The composition can be present in dosage unit form.

The present invention also relates to a passive immunotherapy approach wherein B cells from patients with a primary autoimmune disease, such as systemic lupus erythematosis (SLE) or anti-phospholipid antibody syndrome or patients with infectious diseases such as syphilis, leishmaniasis, and leprosy, are used in the production of cross-reactive antibodies (including monoclonal antibodies other than 4E10 and 2F5). That is, the invention includes the use of B cells from SLE patients, as well as other patients with disordered immunoregulation (that is, patients with a primary autoimmune disease, or a non-HIV infection such as those noted above, that produce autoantibodies cross-reactive with HIV envelope), in the production of immortal cell lines that provide a source of antibodies that cross-react with HIV envelope (such as 2F5-like and 4E10-like antibodies) (see Stiegler et al, AIDS Res. Hum. Retroviruses 17:1757-1765 (2001), Armbruster et al, J. Antimicrob. Chemother. 54:915-920 (2004), U.S. Pat. No. 5,831,034). Advantageously, the B cells are from an SLE patient (or patient with another primary autoimmune disease) that is HIV infected or that has received an envelope-based HIV vaccine (while not wishing to be bound by theory, HIV infection or vaccination may serve to "boost" primed B1 cells (e.g., cardiolipin-primed B1 cells) to produce 2F5- and/or 4E10-like antibodies and escape deletion (which would occur in a normal subject)—the "boost" may trigger somatic hypermutation so that the resulting Ig genes encode antibodies that fit 2F5 and or 4E10-like epitopes—or that fit other gp160 epitopes that induce broadly neutralizing antibodies but are deleted in normal subjects). The production of immortal cell lines from B cells can be effected using any of a variety of art recognized techniques, including, but not limited to, fusing such B cells with myeloma cells to produce hybridomas.

Once selected, sequences encoding such cross-reactive antibodies (or binding fragments thereof) can be cloned and amplified (see, for example, Huse et al, Science 246:1275-1281 (1989), and phage-display technology as described in WO 91/17271, WO 92/01047, U.S. Pat. Nos. 5,877,218, 5,871,907, 5,858,657, 5,837,242, 5,733,743 and 5,565,332). Soluble antibodies for therapy can then be designed and produced using art recognized techniques (Stiegler et al, AIDS Res. Hum. Retroviruses 17:1757-1765 (2001), Armbruster et al, J. Antimicrob. Chemother. 54:915-920 (2004)).

In accordance with this approach, the antibody (or binding fragment thereof) can be administered in doses ranging from about 10 to 100 mg/dose, preferably 25 mg/dose. The dosage and frequency can vary with the antibody (or binding fragment thereof), the patient and the effect sought (see Armbruster et al, J. Antimicrob. Chemother. 54:915-920 (2004)). The antibodies described above can be used prophylactically or therapeutically.

The antibodies (or binding fragments thereof), or DNA encoding the antibodies or binding fragments, can be formulated with a carrier (e.g., pharmaceutically acceptable carrier) and can be administered by, for example, parenteral, intravenous, subcutaneous, intramuscular or intranasal routes.

Finally, animal species such as camels (Ramsland et al, Exp. Clin. Immunogenet. 18:176-198 (2001), Litman et al, Annu. Rev. Immunol. 7:109-147 (1999)). cows (Ramsland et al, Exp. Clin. Immunogenet. 18:176-198 (2001), Litman et al, Annu. Rev. Immunol. 7:109-147 (1999)) and sharks (Ramsland et al, Exp. Clin. Immunogenet. 18:176-198 (2001), Litman et al, Annu. Rev. Immunol. 7:109-147 (1999), Hohman et al, Proc. Natl. Acad. Sci. USA. 90:9882-9886 (1993)) have very long CDR3 lengths, and their antibodies show polyreactivitiy. These engineered CDR3s that show polyreactivity to HIV envelope can be utilized for making potent therapeutic antibodies (e.g, monoclonal antibodies, including, for example, chimeric and humanized antibodies, and antigen binding fragments thereof) to HIV and to many infectious agents.

In a specific embodiment, the present invention further relates to synthetic liposome-peptide conjugates and to methods of using same as immunogens for the generation of broadly neutralizing antibodies against HIV-1. This embodiment of the invention provides compositions and methods for embedding into synthetic liposomes nominal epitope peptides of broadly neutralizing antibodies that bind to the MPER of HIV-1 gp41. Also provided are immunization strategies and protocols for the generation of anti-HIV-1 neutralizing antibodies and for the detection of antigen specific B cell responses.

Figure 7:
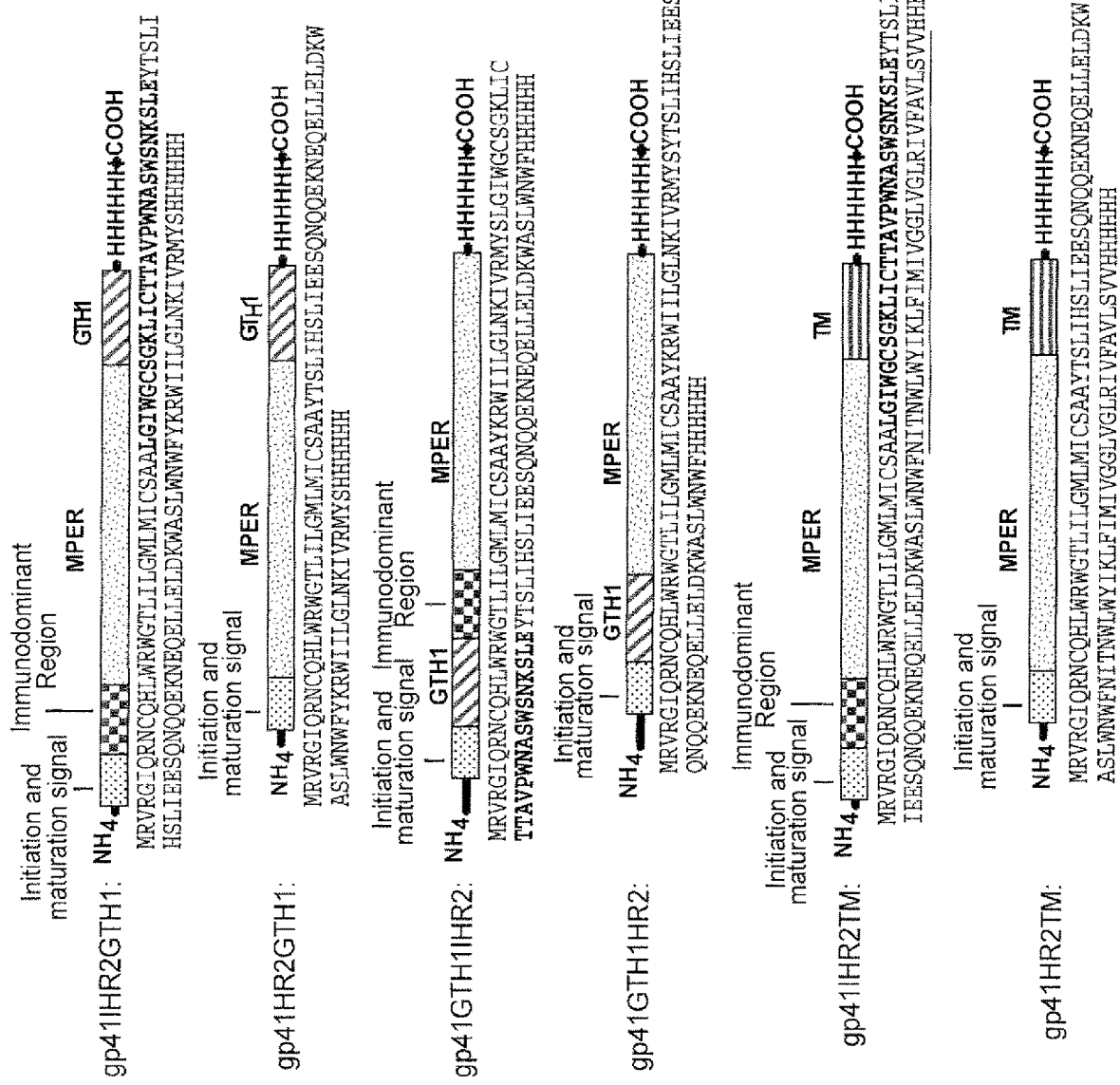
FIG. 7. Schematic presentation of various designs of MPER gp41 constructs. The functional regions are indicated above the schematic constructs. Amino acid sequences are indicated below each of schematic constructs (SEQ ID NO:15-SEQ ID NO:20). Initiation and maturation signal sequences are highlighted in blue; immunodominant regions are highlighted in bold; MPER regions are highlighted in brown and GTH1 domains are highlighted in red and transmembrane domains are underlined. His-tags were added to the C-terminal ends of the constructs for easy purification and are highlighted in green.
Figure 8:
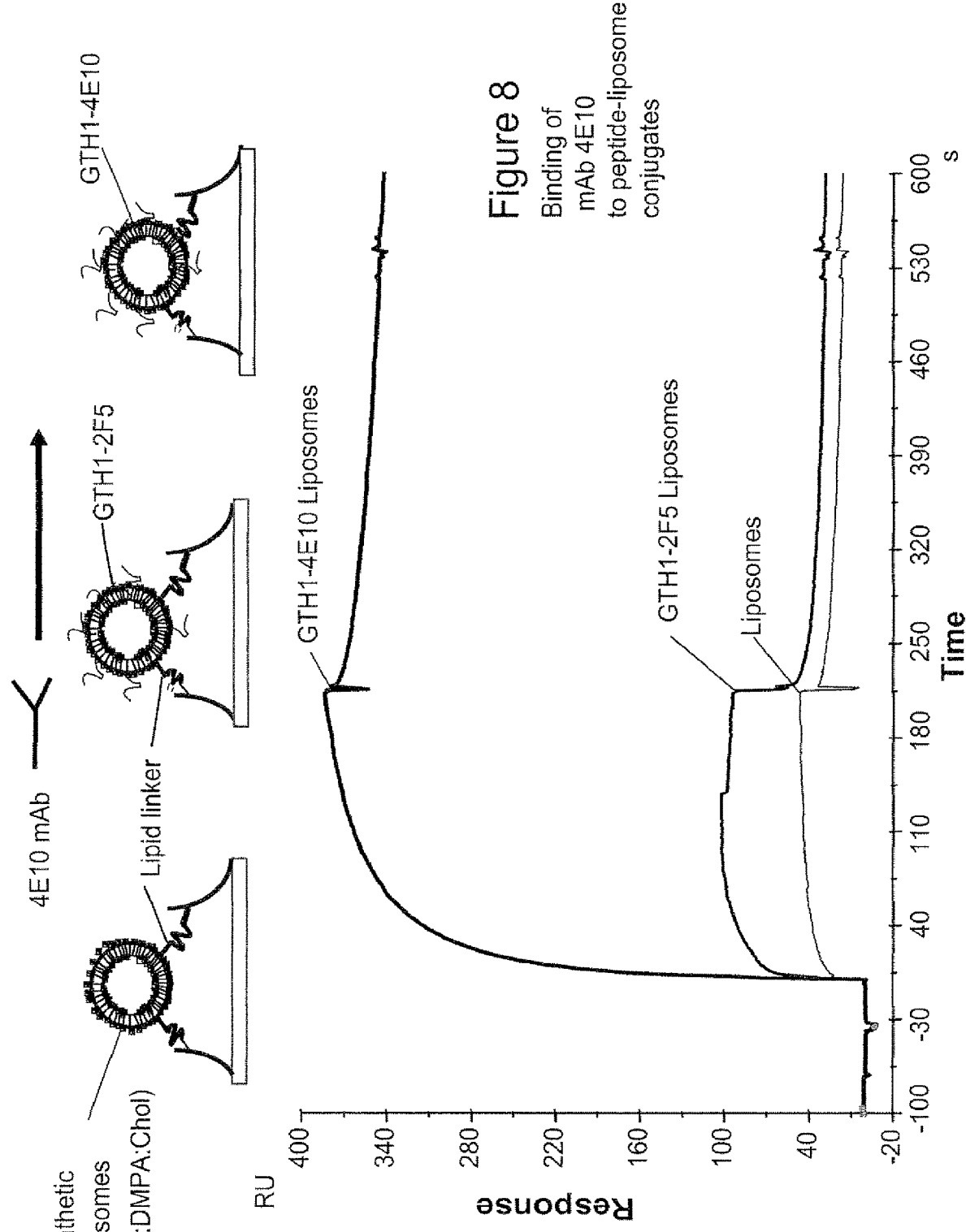
FIG. 8. Binding of mAb 4E10 to peptide-liposome conjugates. BIAcore binding curves show specific and markedly higher binding of mAb 4E10 to GTH1-4E10 liposomes. Low levels of binding with fast kinetics to GTH1-2F5 liposomes were also detected.
Figure 9:
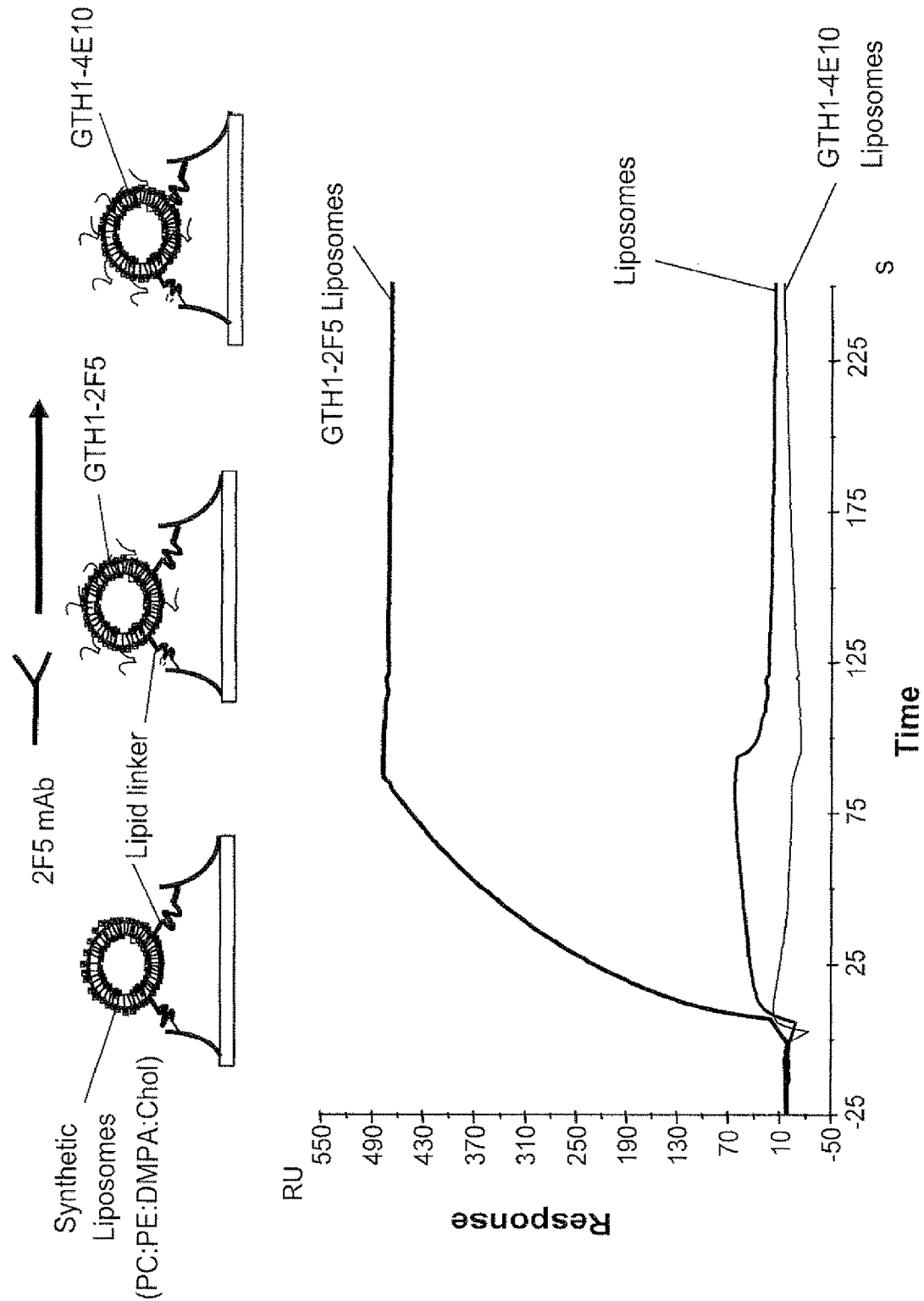
FIG. 9. Binding of 2F5 mAb to peptide-liposomes. MAb 2F5 bound specifically to GTH1-2F5 liposomes and showed no binding to GTH1-4E10 liposomes.
Figure 10:
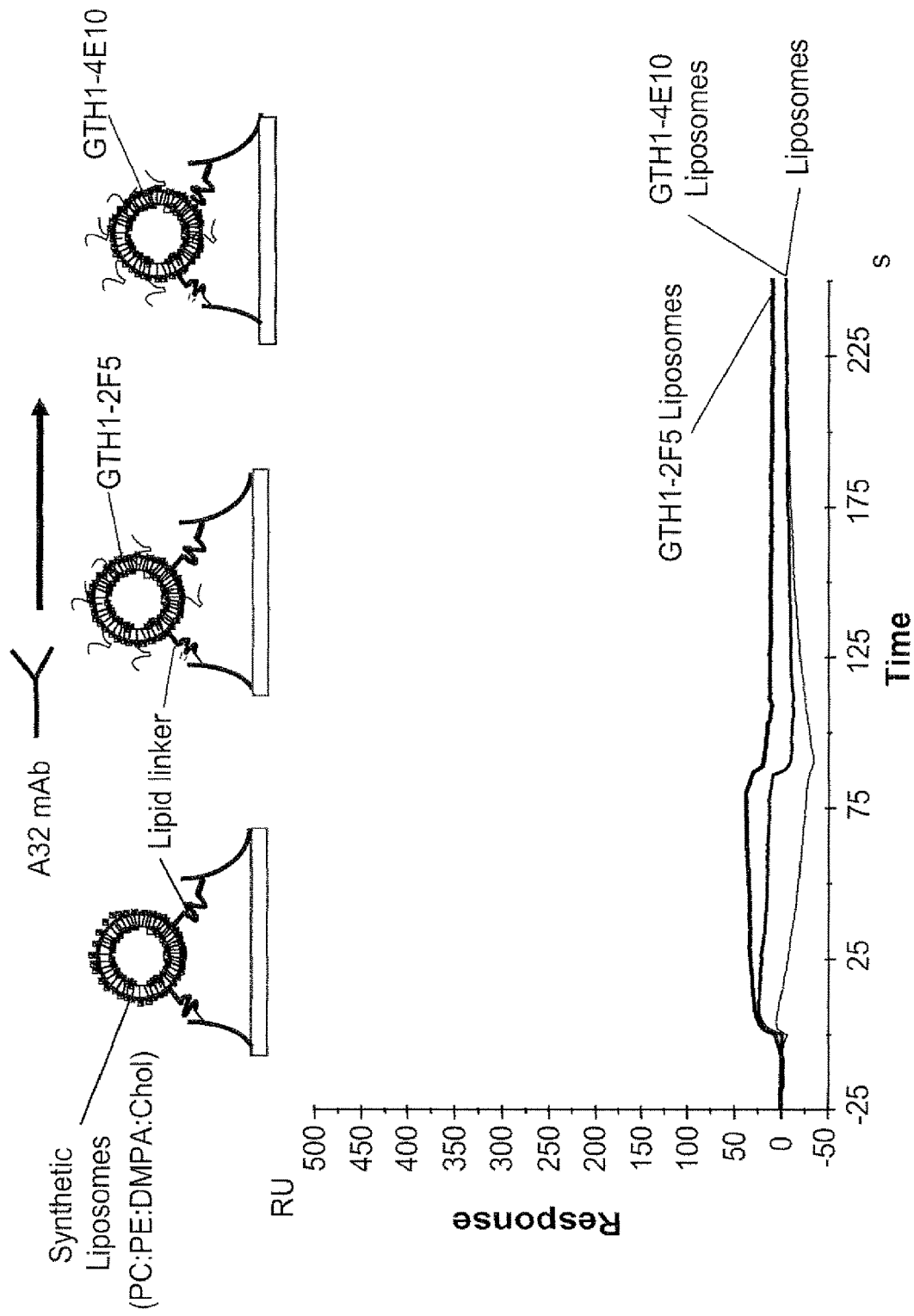
FIG. 10. A32 mAb binding to peptide-liposomes. A control anti-gp120 Mab. A32, showed no binding to any of the liposome conjugates. 17b, a CD4-inducible mAb, also showed no binding to the above liposome conjugates (data not shown).
Figure 11:
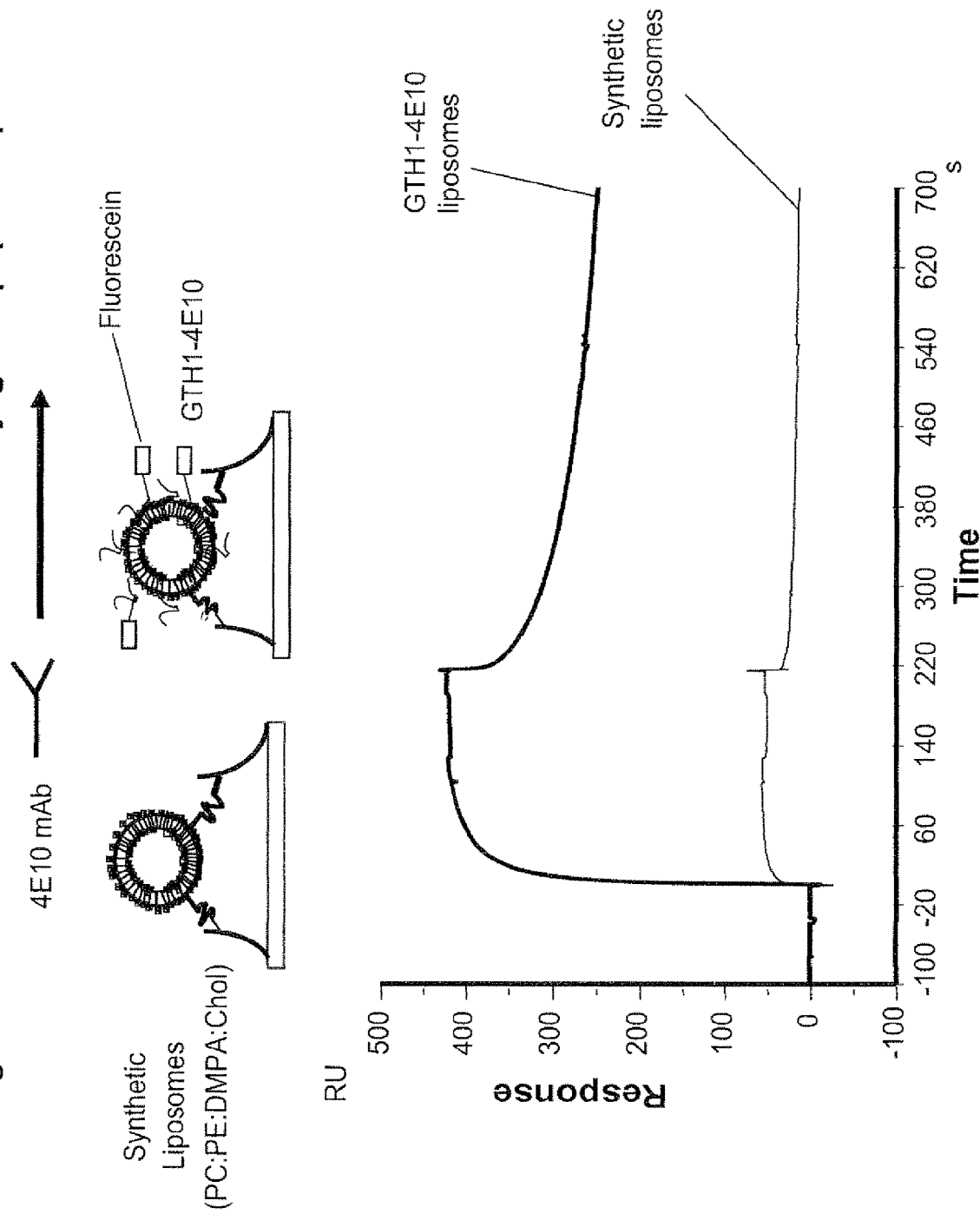
FIG. 11. Generation of fluorescein conjugated peptide-liposomes. Peptide-liposomes were conjugated with a fluorescein tag by incorporating fluorescein-POPE in the lipid composition. Binding assays show that the specificity of mAb 4E10 binding is retained in fluorescein conjugated liposomes. Fluorescein-conjugated GTH1-2F5 liposomes gave similar results.

In accordance with this embodiment of the invention, peptide sequences that include a nominal epitope of a broadly neutralizing anti-HIV antibody and a hydrophobic linker, such as GTH1 (see FIG. 6 for sequence), are embedded into synthetic liposomes. In a preferred aspect, the nominal epitope is that of mAbs 2F5 (ELDKWAS) (SEQ ID NO:12) or 4E10 (WFNITNW) (SEQ ID NO:21), which, as noted above, lie in the MPER of HIV-1 envelope gp41. The epitope can be present in the peptide such that antibodies specific therefor have relatively unconstrained access or, alternatively, the epitope can be present in the peptide in relation to the hydrophobic linker so as to mimic the native orientation of the MPER region. Specific examples of peptide sequences suitable for use in the invention are set forth in FIG. 6. In addition, the MPER gp41 region can be expressed as recombinant proteins in recombinant vaccinia virus, in human cell expression systems, and formulated with amphipathic alpha helices at the N or C termini of the gp41 component for ease in association with liposomes (FIG. 7).

Liposomes suitable for use in the invention include, but are not limited to, those comprising POPC, POPE, DMPA (or sphingomyelin (SM)), lysophosphorylcholine, phosphatidylserine, and cholesterol (Ch). While optimum ratios can be determined by one skilled in the art, examples include POPC:POPE (or POPS):SM:Ch or POPC:POPE (or POPS):DMPA:Ch at ratios of 45:25:20:10. Alternative formulations of liposomes that can be used include DMPC (1,2-dimyristoyl-sn-glycero-3-phosphocholine) (or lysophosphorylcholine), cholesterol (Ch) and DMPG (1,2-dimyristoyl-sn-glycero-3-phoshpho-rac-(1-glycerol) formulated at a molar ratio of 9:7.5:1 (Wassef et al, ImmunoMethods 4:217-222 (1994); Alving et al, G. Gregoriadis (ed.), Liposome technology $2^{nd}$ ed., vol. III CRC Press, Inc., Boca Raton, Fla. (1993); Richards et al, Infect. Immun. 66(6):285902865 (1998)). The above-described lipid compositions can be complexed with lipid A and used as an immunogen to induce antibody responses against phospholipids (Schuster et al, J. Immunol. 122:900-905 (1979)). A preferred formulation comprises POPC:POPS:Ch at ratios of 60:30:10 complexed with lipid A according to Schuster et al, J. Immunol. 122:900-905 (1979). Peptides suitable for inclusion in such a formulation include, but are not limited to, 2F5-GTH1, 4E10-GTH1, SP8926-GTH1, and SP8928-GTH1.

The optimum ratio of peptide to total lipid can vary, for example, with the peptide and the liposome. For the peptides of Example 3, a ratio 1:420 was advantageous.

The above-described liposomes can be admixed with recombinant domain V of ß2 glycoprotein 1 to elicit antibodies against this domain.

The liposome-peptide conjugates can be prepared using standard techniques (see too Examples 3 and 4 that follow).

The peptide-liposome immunogens of the invention can be formulated with, and/or administered with, adjuvants such as lipid A, oCpGs, TRL4 agonists or TLR 7 agonists that facilitate robust antibody responses (Rao et al, Immunobiol. Cell Biol. 82(5):523 (2004)). Other adjuvants that can be used include alum and Q521 (which do not break existing B cell tolerance). Preferred formulations comprise an adjuvant that is designed to break forms of B cell tolerance, such as oCpGs in an oil emulsion such as Emulsigen (an oil in water emulsion) (Tran et al, Clin. Immunol. 109(3):278-287 (2003)). Additional suitable adjuvants include those described in Ser. No. 11/302,505, filed Dec. 14, 2005, including the TRL agonists disclosed therein.

The peptide-liposome immunogens can be administered, for example, IV, intranasally, subcutaneously, intraperitoneally, intravaginally, or intrarectally. The route of administration can vary, for example, with the patient, the conjugate and/or the effect sought, likewise the dosing regimen. The peptide-liposome immunogens are preferred for use prophylactically, however, their administration to infected individuals may reduce viral load.

As described in Example 3 that follows, the peptide-liposome conjugates can be used as reagents for the detection of MPER-specific B cell responses. For example, the peptide-liposome constructs can be conjugated with a detectable label, e.g., a fluorescent label, such as fluorescein. The fluorescein-conjugated liposomes can be used in flow cytometric assays as a reagent for the detection of anti-MPER specific B cell responses in hosts immunized with HIV-1 Env proteins that present exposed MPER region. These reagents can be used to study peripheral blood B cells to determine the effectiveness of immunization for anti-MPER antibody induction by measuring the number of circulating memory B cells after immunization. The data presented in the Examples that follow indicate that conformational change associated binding of HIV-1 cluster 11 monoclonal antibodies to nominal epitope peptide lipid conjugates correlates with HIV-1 neutralization (see Example 5).

It will be appreciated from a reading of the foregoing that if HIV has evolved to escape the host immune response by making the immune system blind to it, other infectious agents may have evolved similarly. That is, this may represent a general mechanism of escape. That being the case, approaches comparable to those described herein can be expected to be useful in the treatment of such other agents well.

Certain aspects of the invention are described in greater detail in the non-limiting Examples that follow (see also Maksyutov et al, J. Clin. Virol. December 31 Suppl 1:S26-38 (2004), US Appln. 20040161429, and Haynes et al, Science 308:1906 (2005)).

Example 1

Design of an HIV-1 immunogen that can induce broadly reactive neutralizing antibodies is a major goal of HIV-1 vaccine development. While rare human mabs exist that broadly neutralize HIV-1, HIV-1 envelope immunogens do not induce these antibody specificities. In this study, it was demonstrated that the two most broadly reactive HIV-1 envelope gp41 human mabs, 2F5 and 4E10, are polyspecific, autoantibodies reactive with cardiolipin. Thus, current HIV-1 vaccines may not induce antibodies against membrane proximal gp41 epitopes because of gp41 membrane proximal epitopes mimicry of autoantigens.

Experimental Details

Monoclonal Antibodies. Mabs 2F5, 2G12, and 4E10 were produced as described (Steigler et al, AID Res. Human Retroviruses 17:1757 (2001), Purtscher et al, AIDS 10:587 (1996), Trkola et al, J. Virol. 70:1100 (1996)). IgG1b12 (Burton et al, Science 266:1024-1027(1994)) was the generous gift of Dennis Burton, Scripps Institute, La Jolla, Calif. Mab 447-52D (Zolla-Pazner et al, AIDS Res. Human Retrovirol. 20:1254 (2004)) was obtained from the AIDS Reagent Repository, NIAID, NIH. The remainder of the mabs in Table 1 were produced from HIV-1 infected subjects and used as described (Robinson et al, AIDS Res. Human Retrovirol. 6:567 (1990), Binley et al, J. Virol. 78:13232 (2004)).

Autoantibody Assays. An anti-cardiolipin ELISA was used as described (DeRoe et al, J. Obstet. Gynecol. Neonatal Nurs. 5:207 (1985), Harris et al, Clin. Exp. Immunol. 68:215 (1987)). A similar ELISA was adapted for assay for mab reactivity to phosphatidylserine, phosphatidylcholine, phosphatidyethanolamine, and sphingomyelin (all purchased from Sigma, St. Louis, Mo.). The Luminex AtheNA Multi-Lyte ANA Test (Wampole Laboratories, Princeton, N.J.) was used for mab reactivity to SS-A/Ro, SS-B/La, Sm, ribonucleoprotein (RNP), Scl-70, Jo-1, double stranded (ds) DNA, centromere B, and histone. Mab concentrations assayed were 150 µg, 50 µg, 15 µg, and 5 µg/ml. Ten µl of each concentration (0.15 µg, 0.05 µg, 0.015 µg, and 0.005 µg, respectively, per assay) were incubated with the Luminex fluorescence beads and the test performed per manufacturer's specifications. Values in Table 1 are results of assays with 0.15 µg added per test. In addition, an ELISA for SS-A/Ro (ImmunoVision, Springdale, Ark.) and dsDNA (Inova Diagnostics, San Diego, Calif.) was also used to confirm these autoantigen specificities. Reactivity to human epithelial Hep-2 cells was determined using indirect immunofluoresence on Hep-2 slides using Evans Blue as a counterstain and FITC-conjugated goat anti-human IgG (Zeus Scientific, Raritan N.J.). Slides were photographed on a Nikon Optiphot fluorescence microscope. Rheumatoid factor was performed by nephelometry (Dade Behring, Inc (Newark, Del.). Lupus anticoagulant assay was performed by activated partial thromboplastin (aPTT) and dilute Russell viper venom testing, as described (Moll and Ortel, Ann. Int. Med. 127:177 (1997)). Fourty µl of 1 mg/ml of 2F5, 4E10 and control mabs were added to pooled normal plasma (final mab concentration, 200 µg/ml) for lupus anticoagulant assay. Anti-132 glycoprotein-1 assay was an ELISA (Inova Diagnostics, Inc.). Serum antibodies to dsDNA, SS-A/Ro, SS-B/La, Sm, RNP and histone occur in patients with SLE; serum antibodies to centromere B and scl-70 (topoisomerase I) are found in systemic sclerosis; and antibodies to Jo-1 are found in association with polymyositis (Rose and MacKay, The Autoimmune Diseases, Third Ed. Academic Press, Sand Diego, Calif. (1998)).

Results

The reactivity of mabs 2F5 and 4E10, two additional rare broadly reactive neutralizing mabs (2G12 and IgG1b12), and thirty-one common anti-HIV-1 Env human mabs, with cardiolipin (Robinson et al, AIDS Res. Human Retrovirol. 6:567 (1990)) was determined (Table 1). Both 2F5 and 4E10 reacted with cardiolipin, whereas all 33 of the other mabs were negative. Mab 2F5 also reacted with SS-A/Ro, histones and centromere B autoantigen, while mab 4E10 reacted with the systemic lupus erythematosus (SLE) autoantigen, SS-A/Ro. Both 2F5 and 4E10 reacted with Hep-2 human epithelial cells in a diffuse cytoplasmic and nuclear pattern (Robinson et al, AIDS Res. Human Retrovirol. 6:567 (1990)) (FIG. 2). Thus, both 2F5 and 4E10 are characterized by polyspecific autoreactivity.

TABLE 1

| Map Type and Antibody Name | Cardiolipin | Hep-2 Cell Reactivity | Ro(SSA) | dsDNA | Centromere B | Histones |
|---|---|---|---|---|---|---|
| Membrane Proximal External Region (2PS) | 47 | +Cytoplasmic nuclear | 290 | — | 1,776 | 1,011 |
| Membrane Proximal External Region (4E10) | 15,434 | +Cytoplasmic nuclear | 221 | — | — | — |
| CD4 Binding Site (IgG1b12) | — | +Cytoplasmic nucleolar | — | 513 | 479 | 185 |
| CD4 Binding Site (F1, 5E, 25G) | — | — | — | — | — | — |
| Adjacent CD4 Binding Site (A32) | — | — | — | — | 1,131 | — |
| Adjacent CD4 Binding Site (1.4G) | — | — | — | 768 | 1,422 | 539 |
| Adjacent CD4 Binding Site (1.4C, 4.6H, 4.11C) | — | — | — | — | — | — |
| Third variable loop (CO11, F2A3, F3-9F, LA21, 447-52D) | — | — | — | — | — | — |
| gp41 Immunodominant region (7B2, KU32) | — | — | — | — | — | — |
| gp41 Immunodominant region (2.2B) | — | +intermediate filament | — | — | 314 | — |
| C1-C4 gp120 (8.2A, 2.3B) | — | — | — | — | — | — |
| C1-C4 gp120 (EH21, C11) | — | — | — | — | — | — |
| Glycan-dependent (2G12) | — | — | — | — | — | — |
| CCR5 binding aite (1.7B, 2.1C, LF17, E51, 1.9F, LA15, 4.8E, LA28, 1.9E, E047, 2.5E, ED10) | — | — | — | — | — | — |
| Positive control serum | 34 | +homogeneous nuclear | 1385 | 228 | 624 | 34 |
| Negative controls | <16 | — | <120 | <120 | <120 | <120 |

All Mabs were negative in assays for reactivity with La (SSB), Sm, Scl-79 and Jo-1, except for Ku32 mab that reacted with Sm, Ro (SSA), dsDNA, centromers B. histone and cardiolipin antibody values are in relative units based on a standard cure − = negative Of the two other rare neutralizing mabs, one mab, 2G12, was not autoreactive, while another mab against the CD4 binding site, IgG1b12 (Stiegler et al, AIDS Res. Hum. Retroviruses 17:1757 (2001)), reacted with ribonucleoprotein, dsDNA, and centromere B as well as with Hep-2 cells in a cytoplamic and nucleolar pattern (Table 1 and FIG. 2). Of the 31 more common anti-HIV-1 mabs studied, only two mabs with specificity for binding near the CD4 binding site (A32, 1.4G) and a mab to a non-neutralizing gp41 epitope (2.2 B) showed evidence of polyreactivity (Table 1).

To determine if 2F5 and 4E10 were similar to prothrombotic anti-cardiolipin antibodies found in SLE-associated anti-phospholipid syndrome (Burton et al, Science 266: 1024-1027 (1994)), both mabs were tested for lupus anticoagulant activity, and for the ability to bind to prothombin (PT), beta-2 glycoprotein-1, phosphatidylserine (PS), phosphatidylcholine (PC), phosphatidylethanolamine (PE), and sphingomyelin (SM) (Robinson et al, AIDS Res. Human Retrovirol. 6:567 (1990)). Whereas 2F5 was negative for these reactivities, 4E10 had lupus anticoagulant reactivity, and reacted strongly with PS, PC, PE, weakly with SM and PT, and negatively with P2 glycoprotein-1. (See FIG. 3.)

Anti-cardiolipin antibodies can be found in patients with disordered immunoregulation due to autoimmune disease or infection (Burton et al, Science 266:1024-1027 (1994)). Anti-cardiolipin autoantibodies are induced by syphilis, leprosy, leishmaniasis, Epstein Barr virus, and HIV-1 (Burton et al, Science 266:1024-1027 (1994)). Unlike anti-cardiolipin antibodies found in SLE, "infectious" anti-cardiolipin antibodies are rarely prothrombotic, and are transient. Thus, 4E10 is similar to anti-cardiolipin antibodies in autoimmune disease, and 2F5 is similar to anti-cardiolipin antibodies in infectious diseases.

Autoreactive B cell clones with long CDR3 lengths are normally deleted or made tolerant to self antigens ((Zolla-Pazner et al, AIDS Res. Human Retrovirol. 20:1254 (2004)). Thus, HIV-1 may have evolved to escape membrane proximal antibody responses by having conserved neutralizing epitopes as mimics of autoantibody epitopes. These data suggest that current HIV-1 vaccines do not routinely induce robust membrane proximal anti-envelope neutralizing antibodies because antibodies targeting these epitopes are derived from autoreactive B cell clones that are normally deleted or made tolerant upon antigenic stimulation by HIV-1 Env. These observations may also explain the rare occurrence of HIV-1 in SLE patients who may be unable to delete such clones (Fox et al, Arth. Rhum. 40:1168 (1997)).

Example 2

The ability of autoantigens of the invention to induce the production of neutralizing antibodies was studied using, as autoantigen, cardiolipin (lamellar and hexagonal phases), 1-palmitoyl-2-oleoyl-sn-glycero-3-[phospho-L-serine] (POPS) (lamellar and hexagonal phases), 1-palmitoyl-2-oleoyl-phosphatidylethanolamine (POPE) (lamellar phase) and dioleoyl phosphatidylethanolamine (DOPE) (hexagonal phase). Guinea pigs (4 per group) were immunized with phospholopid (cardiolipin lamellar phase, cardiolipin hexagonal phase, POPS lamellar phase, POPS hexagonal phase, POPE lamellar phase or DOPE hexagonal phase) in 10 µg of oCpGs, four times, with each immunization being two weeks apart. Following the four phospholipid immunizations, a final immunization was made IP with 10 µg of oCpGs with 100 µg of group M consensus Env, CON-S gp140CFI oligomer (that is, the CFI form of the protein shown in FIG. 4A).

Neutralization assays were performed using an Env pseudotype neutralization assay in TMZ cells (Wei et al, Nature 422:307-312 (2003), Derdeyn et al, J Virol 74:8358-8367 (2000). Wei et al, Antimicrob Agents Chemother 46:1896-1905 (2002), Platt et al, J Virol 72:2855-2864 (1998), Mascola et al, J. Virol. 79:10103-10107 (2005)), as described below:

Cell Culture

TZM-bl is an adherent cell line and is maintained in T-75 culture flasks. Complete growth medium (GM) consists of D-MEM supplemented with 10% fetal bovine serum (FBS, heat-inactivated) and gentamicin (50 µg/ml). Cell monolayers are disrupted and removed by treatment with trypsin/EDTA:

Trypsin-EDTA Treatment for Disruption of TZM-bl Cell Monolayers:

Cell monolayers maintained in T-75 culture flasks are disrupted and removed by treatment with trypsin/EDTA at confluency when splitting cells for routine maintenance and when preparing cells for assay.

1. Decant the culture medium and remove residual serum by rinsing monolayers with 6 ml of sterile PBS.
2. Slowly add 2.5 ml of an 0.25% Trypin-EDTA solution to cover the cell monolayer. Incubate at room temp for 30-45 seconds. Decant the trypsin solution and incubate at 37. degree. C. for 4 minutes. Do not agitate the cells by hitting or shaking the flask while waiting for the cells to detach.
3. Add 10 ml of GM and suspend the cells by gentle pipet action. Count cells.
4. Seed new T-75 culture flasks with approximately 106 cells in 15 ml of GM. Cultures are incubated at 37. degree. C. in a 5% $CO_2$/95% air environment. Cells should be split approximately every 3 days. Virus Stocks Stocks of uncloned viruses may be produced in either PBMC or T cell lines. Pseudoviruses may be produced by transfection in an appropriate cell type, such as 293T cells. All virus stocks should be made cell free by low speed centrifugation and filtration (0.45-micron) and stored at −80. degree. C. in GM containing 20% FBS.

TCID50 Determination

It is necessary to determine the TCID50 of each virus stock in a single-cycle infection assay (2-day incubation) in TZM-bl cells prior to performing neutralization assays. A cut-off value of 2.5-times background RLU is used when quantifying positive infection in TCID50 assays.

Too much virus in the neutralization assay can result in strong virus-induced cytopathic effects that interfere with accurate measurements. Most virus stocks must be diluted at least 10-fold to avoid cell-killing. A standard inoculum of 200 TCID50 was chosen for the neutralization assay to minimize virus-induced cytopathic effects while maintaining an ability to measure a 2-log reduction in virus infectivity. It should be noted that different strains vary significantly in their cytopathicity. Virus-induced cytopathic effects may be monitored by visual inspection of syncytium formation under light microscopy. Cytopthic effects may also be observed as reductions in luminescence at high virus doses in the TCID50 assay.

Neutralizing Antibody Assay Protocol

NOTE 1: All incubations are performed in a humidified 37. degree. C., 5% $CO_2$ incubator unless otherwise specified.

NOTE 2: Assays with replication-competent viruses are performed in DEAE-GM containing 1 µM indinavir.

1. Using the format of a 96-well flat-bottom culture plate, place 150 µl of GM in all wells of column 1 (cell control). Place 100 µl in all wells of columns 2-11 (column 2 will be the virus control). Place an additional 40 µl in all wells of columns 3-12, row H (to receive test samples).
2. Add 11 µl of test sample to each well in columns 3 & 4, row H. Add 11 µl of a second test sample to each well in columns 5 & 6, row H. Add 11 µl of a third test sample to each well in columns 7 & 8, row H. Add 11 µl of a fourth test sample to each well in columns 9 & 10, row H. Add 11 µl of a fifth test sample to each well in columns 11 & 12, row H. Mix the samples in row H and transfer 50 µl to row G. Repeat the transfer and dilution of samples through row A (these are serial 3-fold dilutions). After final transfer and mixing is complete, discard 50 µl from the wells in columns 3-12, row A into a waste container of disinfectant.
3. Thaw the required number of vials of virus by placing in an ambient temperature water bath. When completely thawed, dilute the virus in GM to achieve a concentration of 4,000 $TCID_{50}$/ml.

Cell-free stocks of virus should be prepared in advance and cryopreserved in working aliquots of approximately 1 ml.

4. Dispense 50 µl of cell-free virus (200 $TCID_{50}$) to all wells in columns 2-12, rows A through H. Mix by pipet action after each transfer. Rinse pipet tips in a reagent reservoir containing 40 ml sterile PBS between each transfer to avoid carry-over.
5. Cover plates and incubate for 1 hour.
6. Prepare a suspension of TZM-bl cells (trypsinize approximately 10-15 minutes prior to use) at a density of $1 \times 10^5$ cells/ml in GM containing DEAE dextran (37.5 µg/ml). Dispense 100 µl of cell suspension (10,000 cells per well) to each well in columns 1-12, rows A though H. Rinse pipet tips in a reagent reservoir filled with sterile PBS between each transfer to avoid carry-over. The final concentration of DEAE dextran is 15 µg/ml.
7. Cover plates and incubate for 48 hours.
8. Remove 150 µl of culture medium from each well, leaving approximately 100 µl. Dispense 100 µl of Bright Glo™. Reagent to each well. Incubate at room temperature for 2 minutes to allow complete cell lysis. Mix by pipet action (at least two strokes) and transfer 150 µl to a corresponding 96-well black plate. Read the plate immediately in a luminometer.
9. Percent neutralization is detect lined by calculating the difference in average RLU between test wells (cells+serum sample+virus) and cell control wells (cells only, column 1), dividing this result by the difference in average RLU between virus control (cell+virus, column 2) and cell control wells (column 1), subtracting from 1 and multiplying by 100. Neutralizing antibody titers are expressed as the reciprocal of the serum dilution required to reduce RLU by 50%.

As shown in FIG. 5, animals receiving DOPE (hexagonal phase) had a neutralization titer of 170.

Example 3

Immunogen Design

Peptide sequences that include the nominal epitopes of mAbs 2F5 and 4E10, respectively, linked to a hydrophobic linker (GTH1) were synthesized and embedded into synthetic liposomes (FIG. 6). The first generation of immunogens was designed with the 2F5 and 4E10 epitope sequences at the distal end of the lipid bilayer (FIG. 6A). These constructs provided unconstrained access of mAbs to their respective epitopes. The second generation constructs have been designed to mimic the native orientation of the MPER region with the 2F5 and 4E10 mAb epitope sequences linked proximal to the hydrophobic linker (FIGS. 6A, 6B).

The composition of the synthetic liposomes comprised the following phospholipids, POPC (1-Palmitoyl-2-Oleoyl-sn-Glycero-3-Phosphocholine). POPE (1-Palmitoyl-2-Oleoyl-sn-Glycero-3-Phosphoethanolamine), DMPA (1,2-Dimyristoyl-sn-Glycero-3-Phosphate), and Cholesterol dissolved in chloroform (purchased from Avanti Polar Lipids (Alabaster, Ala.).).

Synthetic liposomes were prepared by dispensing appropriate molar amounts of phospholipids (POPC:POPE:DMPA:Ch=45:25:20:10) in chloroform resistant tubes. The phospholipids were mixed by vortexing and the mixture was dried in the fume hood under a gentle stream of nitrogen. Any residual chloroform was removed by storing the lipids under a high vacuum (15 h). Aqueous suspensions of phospholipids were prepared by adding PBS or TBS buffer, pH 7.4, and incubating at 37. degree. C. for 10-30 minutes, with intermittent, vigorous vortexing to resuspend the phospholipids. The milky, uniform suspension of phospholipids was then sonicated in a bath sonicator (Misonix Sonicator 3000, Misonix Farmingdale, N.Y.). The sonicator was programmed to run 3 consecutive cycles of 45 seconds of total sonication per cycle. Each cycle included 5 seconds of sonication pulse (70 watts power output) followed by a pulse off period of 12 seconds. At the end of sonication, the suspension of lamellar liposomes was stored at 4. degree. C.

HIV-1 MPER peptides GTH1-2F5 and GTH1-4E10 (FIG. 6) were dissolved in 70% chloroform, 30% methanol. Chloroform solutions of lipids were added to the peptide solution, in the molar ratios of 45:25:20:10 (POPC:POPE:DMPA:Cholesterol). Each peptide was added to a ratio of peptide: total phospholipids of 1:420. The mixture was vortexed, then dried and resuspended as described above.

Binding assays to test specificity of mAb binding to each peptide-lipid conjugate were performed following capture of the liposomes on a BAcore L1 sensor chip, which allows immobilization of lipid bilayer via a hydrophobic linker. 2F5, 4E10 and control mAbs (A32 or 17b) were injected over each of the sensor surfaces with either synthetic liposomes, or peptide-lipid conjugates and the binding monitored on a BIAcore 3000 instrument (FIGS. 8-11).

Immunization Strategy

Figure 12:
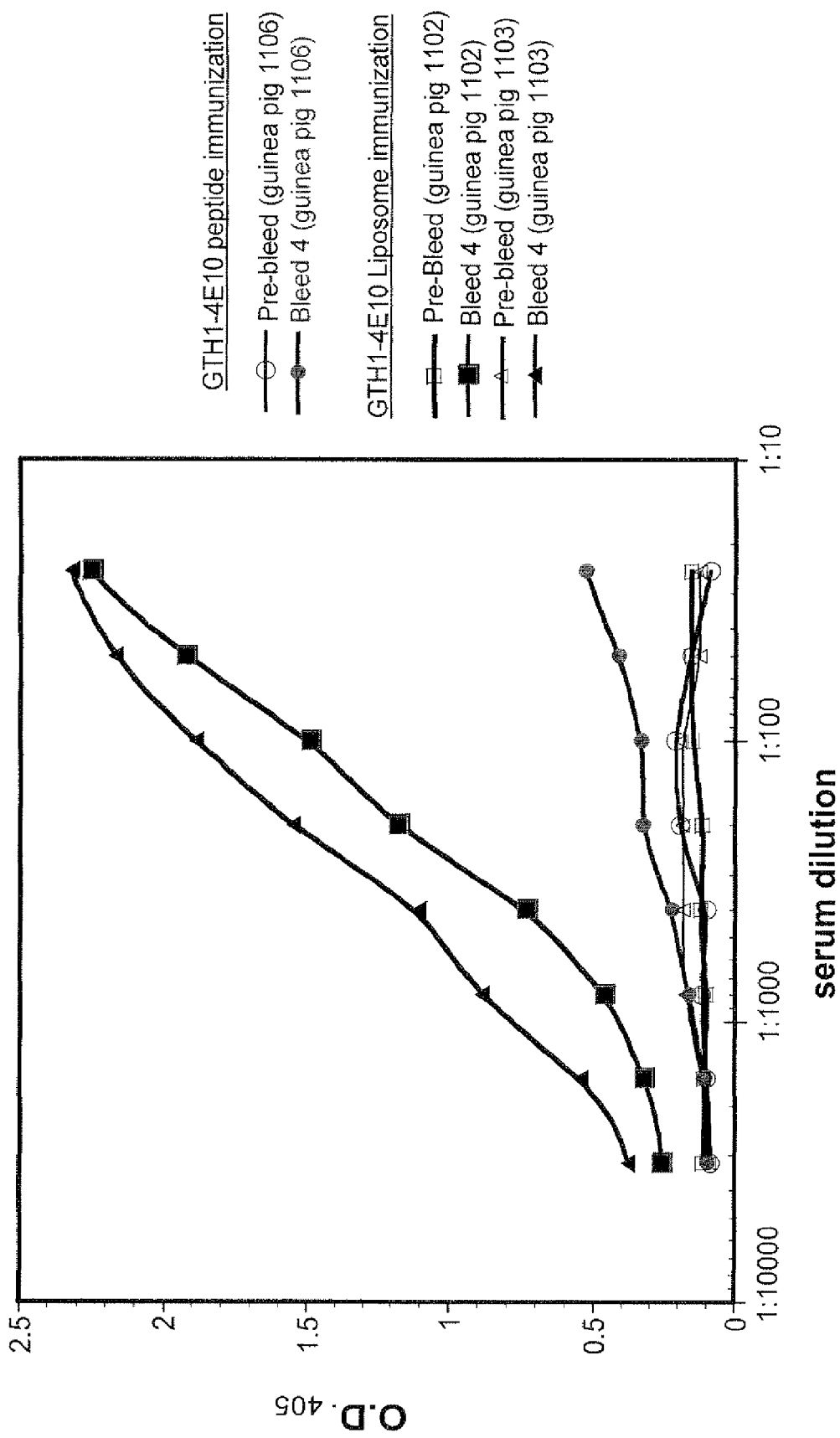
FIG. 12. Reactivity of immunized guinea pig sera with 4E10 peptide. ELISA binding assay show strong positive reactivity of sera to 4E10 peptide from two guinea pigs immunized with GTH1-4E10 liposomes. All pre-bleed sera gave background binding while a low level of binding was observed in a serum from an animal immunized with 4E10 peptide. Both the positive sera from the peptide-liposome immunized animals also showed ne nominal epitope peptide (SP62) was anchored on streptavidin coated BIAcore sensor chip (SA) and either 2F5 mab or 2F5 Fab was injected over the peptide surfaces. Specific binding of 2F5 mAb (46.6-1800 nM) or 2F5 Fab (120-2000 nM) was derived following subtraction of non-specific signal on a HR-1 peptide control surface. Kd was calculated following global curve fitting to a simple Langmuir equation using the BIAevaluation software.
Figure 13:
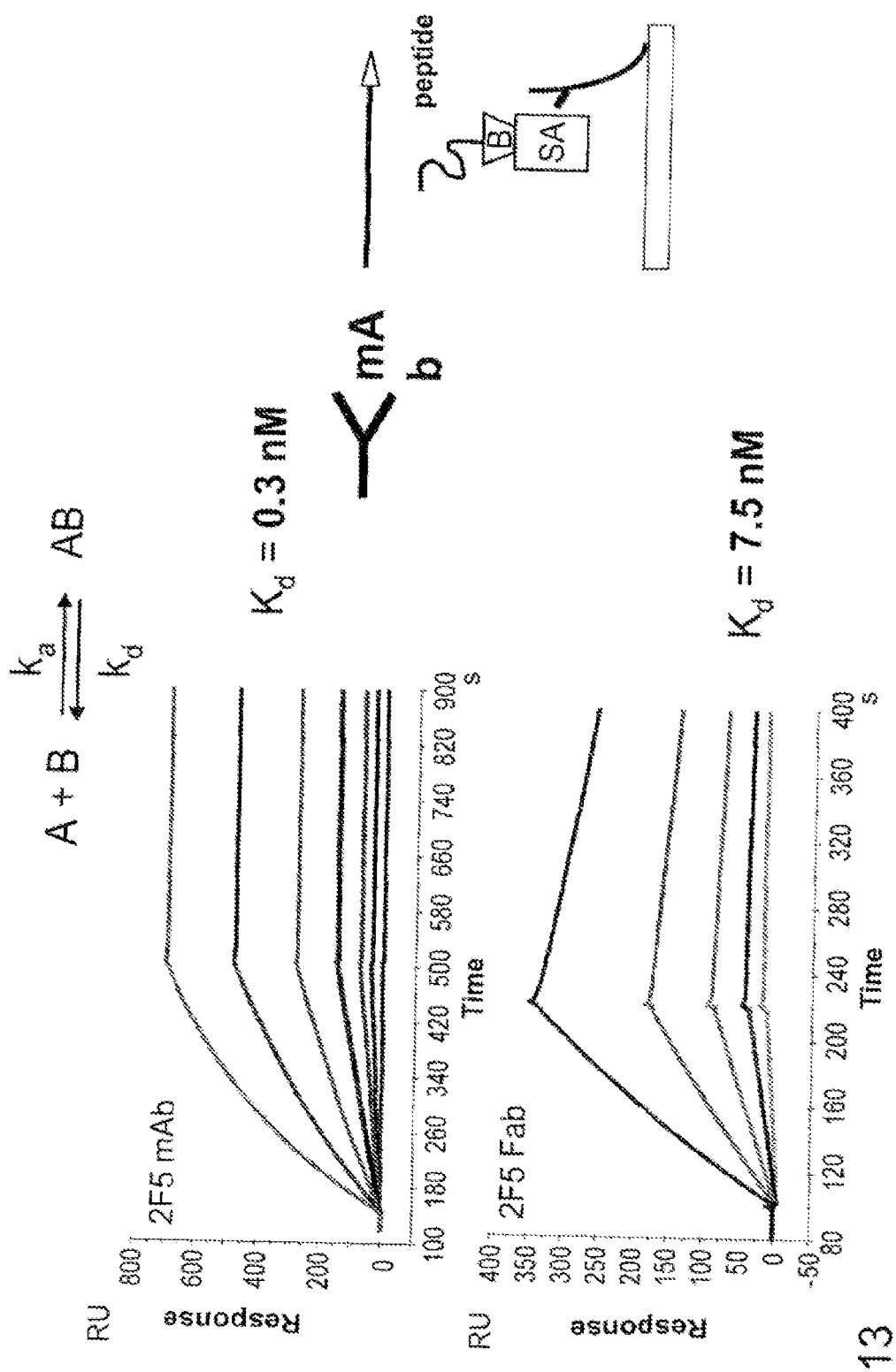

The immunization strategy incorporated a regimen that allows temporary breaks in tolerance. The protocol involves the use of oCpGs, the TLR9 ligand that has been used to break tolerance for the production of anti-dsDNA antibodies in mice (Tran et al, Clin. Immunol. 109(3):278-287 (2003)). The peptide-liposome conjugates were mixed (1:1) with the adjuvant, Emulsigen plus oCpG. The Emulsigen mixed adjuvant (2×) was prepared by mixing 375 μL of Emulsigen, 250 μL of oCpG and 625 μL of saline. Each guinea pig was immunized on a 21-day interval with 250 μg of either peptide alone or peptide-liposome conjugates with equivalent amount of peptide. Serum samples were harvested as pre-bleed prior to first immunization and at each subsequent immunizations. Serum samples were analyzed by ELISA assay (FIG. 12) for binding to peptide epitopes and for viral neutralization assay (Table 2). Data in FIG. 12, show strong reactivity to 4E10 peptide of sera from two guinea pigs immunized with GTH1-4E10 liposomes, while only low level of reactivity was observed in a serum from 4E10 peptide immunized animal. Both the positive sera also neutralized HIV-1 MN strain (Table 2).

TABLE 2

Induction of neutralizing antibodies in guinea pigs immunized with 4E10 peptide-liposomes

Figure 14:
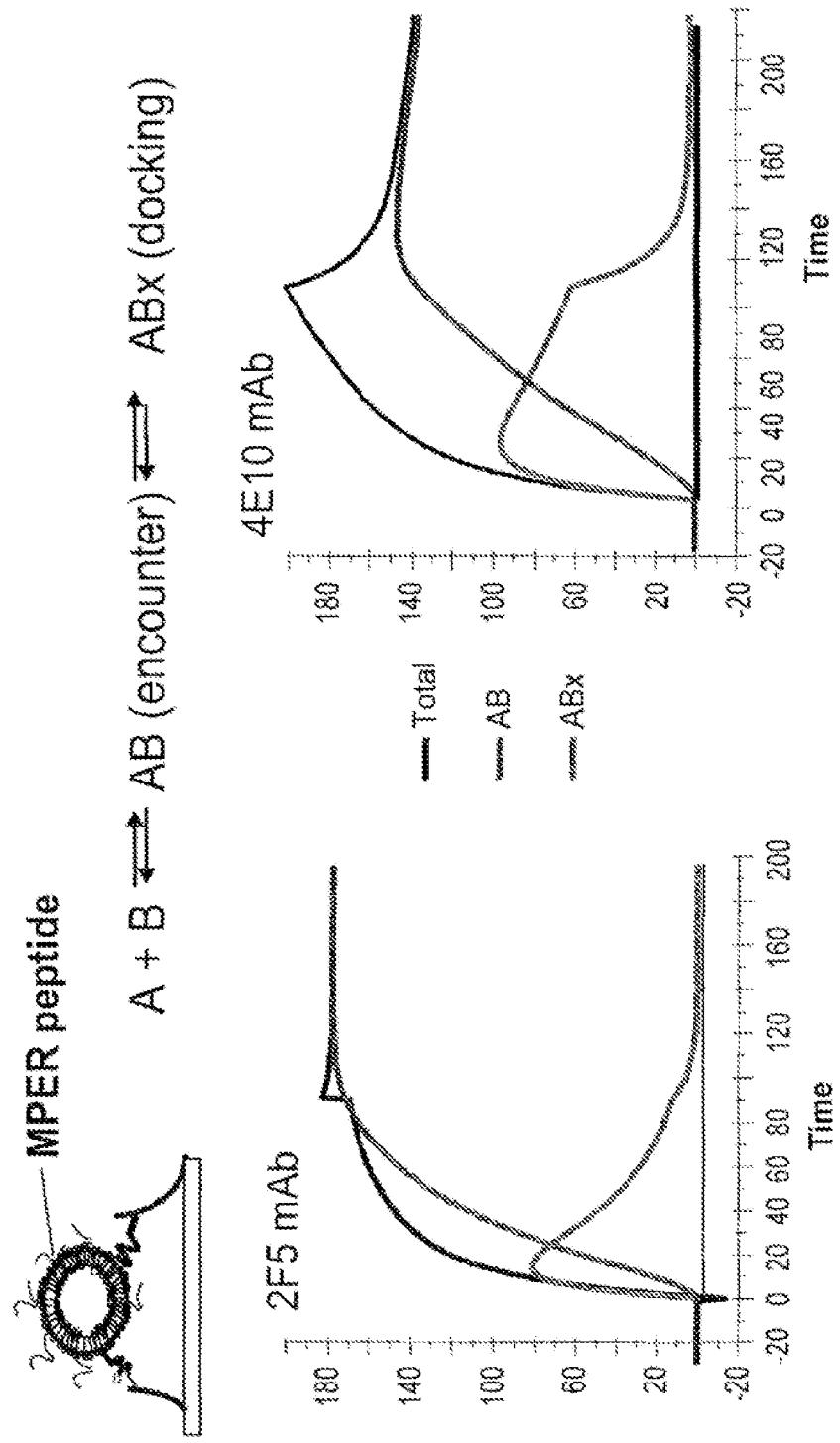
FIG. 14. Neutralizing MPER mAb binding to epitope peptide-lipid conjugate follows a 2-step conformational change model. Binding of 2F5 and 4E10 mAbs to peptide-lipid conjugates is best described by a 2-step conformational change model. About 600 RU of either 2F5 peptide-lipid (left panel) or 4E10 peptide-lipid conjugates were anchored to a BIAcore L1 sensor chip and then 2F5 mAb or 4E10 mAb was injected at 100 ug/mL Curve fitting analysis show that binding of both Mab bound to peptide-lipid conjugates follow a 2-step conformational change mode. In each of the overlay, the binding data is shown in black and represents the observed total binding response. The component curves for the encounter complex (red) and the docked complex (blue) were simulated from the experimentally determined rate constants.

| | HIV-1 Strain/antibody titer | |
|---|---|---|
| Animal No. | MN | SS1196 |
| 1102 Bleed 4 | 209 | 32 |
| 1103 Bleed 4 | 60 | <20 |

Application of Peptide-Liposome Conjugates in the Detection of Antigen Specific B Cell Responses.

The above peptide-liposome conjugates have been utilized as a reagent for the detection of MPER specific B cell responses. The peptide-liposome constructs (2F5 and 4E10) were conjugated with fluorescein by incorporating fluorescein-POPE in the lipid composition. The flourescein-POPE was mixed with unonjugated POPE at a ratio of 45:55 and then mixed with the rest of the lipids in the molar ratio as described above. In BIAcore binding assays, both fluorescein conjugated 2F5 and 4E10-peptide-liposomes retained their specificity in binding to their respective mAbs (FIG. 11).

Example 4

Generation of Peptide-Lipid Conjugates.

Phospholipids POPC (1-Palmitoyl-2-Oleoyl-sn-Glycero-3-Phosphatidylcholine), POPE (1-Palmitoyl-2-Oleoyl-sn-Glycero-3-Phosphatidylethanolamine), DOPE (1,2-Dioleoyl-sn-Glycero-3-Phosphatidylethanolamine); DM PA (1,2-Dimyristoyl-sn-Glycero-3-Phosphate) and cholesterol dissolved in chloroform were purchased from Avanti Polar Lipids (Alabaster, Ala.). Phospholipid liposomes were prepared by dispensing appropriate molar amounts of phospholipids in chloroform resistant tubes. Chloroform solutions of lipids were added to the peptide solution, in molar ratios of 45:25:20:10 (POPC:POPE:DMPA:Cholesterol). HIV-1 membrane proximal peptides were dissolved in 70% chloroform, 30% methanol. Each peptide was added to a molar ratio of peptide:total phospholipids of 1:420. The phospholipids were mixed by gentle vortexing and the mixture was dried in the fume hood under a gentle stream of nitrogen. Any residual chloroform was removed by storing the lipids under a high vacuum (15 h). Aqueous suspensions of phospholipids were prepared by adding PBS or TBS buffer, pH 7.4 and kept at a temperature above the Tm for 10-30 minutes, with intermittent, vigorous vortexing to resuspend the phospholipids followed by Sonication in a bath sonicator (Misonix Sonicator 3000, Misonix Inc., Farmingdale, N.Y.). The sonicator was programmed to run 3 consecutive cycles of 45 seconds of total sonication per cycle. Each cycle included 5 seconds of sonication pulse (70 watts power output) followed by a pulse off period of 12 seconds. At the end of sonication, the suspension of lamellar liposomes was stored at 4. degree. C. and was thawed and sonicated again as described above prior to capture on BIAcore sensor chip.

Design of Peptide-Lipid Conjugates.

Peptides were synthesized and purified by reverse-phase HPLC and purity was confirmed by mass spectrometric analysis. Peptides used in this study include the following—HIV-1 gp41 2F5 epitope peptides—2F5-GTH1 (QQEKNEQELLELDKWASLWN-YKRWIIL-GLNKIVRMYS) (SEQ ID NO:13); and HIV-1 gp41 4E10 epitope peptides—4E10-GTH1 (SLWNWFNITNWL-WYIK-YKRWIILGLNKIVRMYS) (SEQ ID NO:6). Additional peptides to be incorporated into liposomes include—SP8926-GTH1 (EQELLELDKWASLWN-YKRWIILGLNKIVRMYS) (residues 6-37 of SEQ ID NO:13); and Sp8928-GTH1 (KWASLWNWFDITNWL-YKRWIILGLNKIVRMYS) (SEQ ID NO:28).

Peptide-Lipid Conjugates.

Each of these peptides will be incorporated into synthetic liposomes of varying composition which include:

i) POPC:POPE:DMPA:Cholesterol ii) POPC:POPS iii) POPC:POPS:lysoPC iv) POPC:POPE:Sphingomyelin:Cholesterol The liposomes will be complexed with and without monophosphoryl Lipid A (Avanti Polar Lipids).

Example 5

Biotinylated 2F5 nominal epitope peptide (SP62) was anchored on streptavidin coated BIAcore sensor chip (SA) and either 2F5 mab or 2F5 Fab was injected over the peptide surfaces. Specific binding of 2F5 mAb (46.6-1800 nM) or 2F5 Fab (120-200 nM) was derived following subtraction of non-specific signal on a HR-1 peptide control surface. Kd was calculated following global curve fitting to a simple Langmuir equation using the BIAevaluation sortware. The data presented in FIG. 13 show that MPER mAb binding to peptide epitope follows a simple model (Langmuir equation).

About 600 RU of either 2F5 peptide-lipid (FIG. 14, left panel) or 4E10 peptide-lipid conjugates were anchored to a BIAcore L1 sensor chip and then 2F5 mAb or 4E10 mAb was injected at 100 μg/mL. Curve fitting analysis show that binding of both Mab bound to peptide-lipid conjugates follow a 2-step conformational change mode (FIG. 14). In each of the overlay, the binding data is shown in black and represents the observed total binding response. The component curves for the encounter complex (red) and the docked complex (blue) were simulated from the experimentally determined rate constants.

Figure 15:
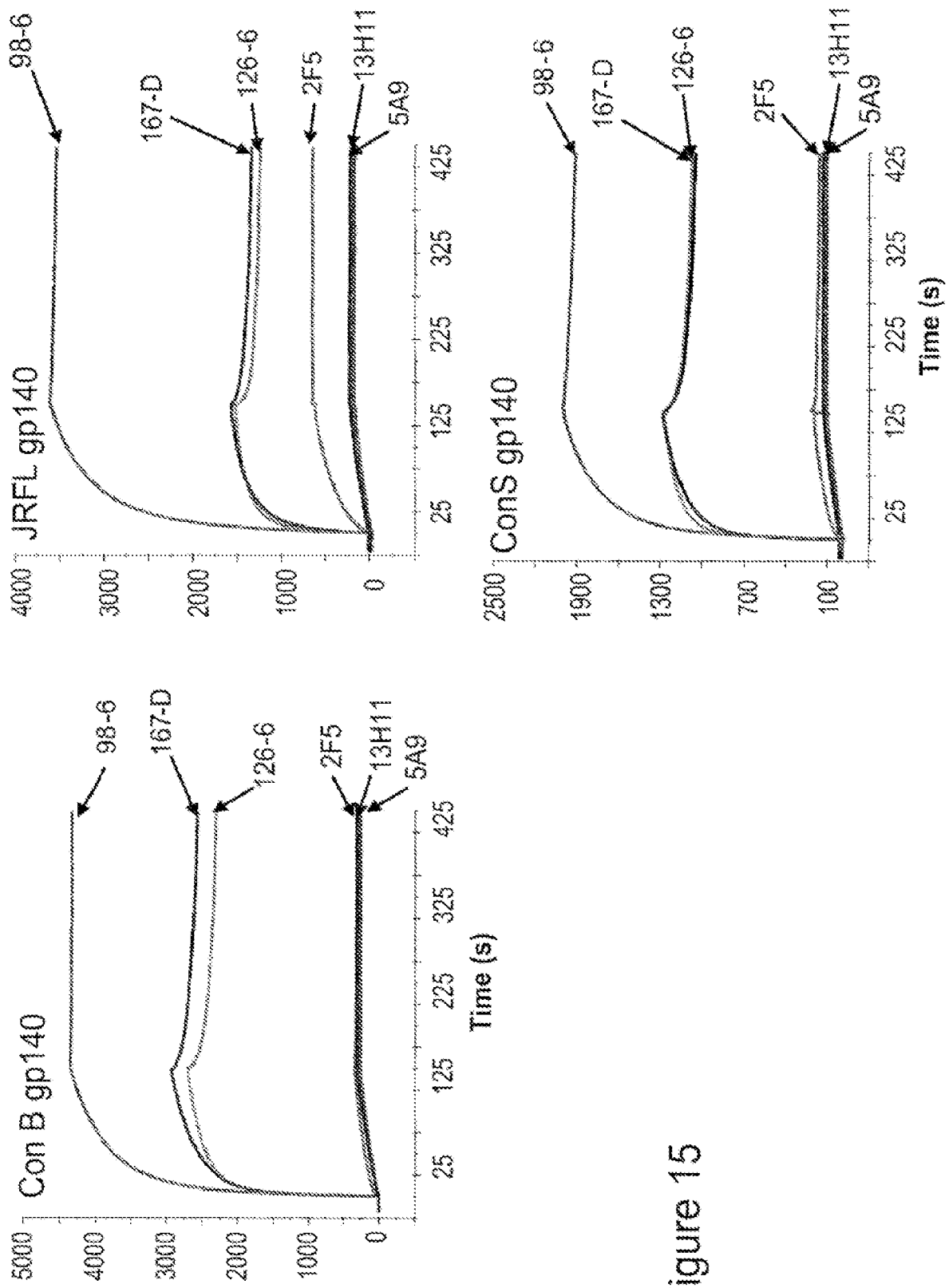
FIG. 15. Human cluster II mAbs (98-6, 167-D, 126-6) bind strongly to Env gp140. Envelope gp140 oligomers were anchored on a BIAcore CM5 chip and each of the indicated mAbs were injected over each of the Env surfaces. Human cluster II mAbs. 98-6, 126-6, and 167-D bound strongly to Env gp 140, while no binding was detected with the non-neutralizing murine MPER mAbs, 2F5. and 4E10.

Envelope gp140 oligomers were anchored on a BIAcore CM5 chip and each of the mAbs indicated in FIG. 15 were injected over each of the Env surfaces. Human cluster 11 mAbs, 98-6,126-6, and 167-D bound strongly to Env gp140, while no binding was detected with the non-neutralizing murine MPER mAbs, 2F5, and 4E10.

Synthetic liposomes (PC:PE; green), or cardiolipin (red) was anchored on a BIAcore L1 sensor chip through hydrophobic interactions with the lipid linker (FIG. 16). Each of the indicated mAbs (500 nM) was injected over each of the lipid surface and a blank control surface. Strong binding of Cluster II mAb 98-6 and 167-D and moderate binding of mAb 126-6 is shown (FIGS. 16A-C). No binding of the anti-MPER mAb 13H11 to either lipid was observed.

2F5-peptide (SP62) lipid conjugates were anchored to a BIAcore L1 surface and binding to mAb 98-6, 167-D or 126-6 was monitored (FIG. 17A). Mab 98-6 bound strongly to the peptide-lipid conjugates, while relatively lower avidity binding was detected with mAb 167-D and 126-6. Curve fitting analysis show a 2-step conformational change associated binding of 2F5 (FIG. 17B) and 98-6 (FIG. 17C); while the binding of mAbs 167-D (FIG. 17D) and 126-6 (FIG. 17E) followed a simple model (Langmuir equation).

The data presented in Table 3 show binding and neutralization characteristics of 25F and other prototype anti-MPER cluster II mAbs. Only mAb 2F5 and 98-6, which bound strongly to linear epitope peptide and followed a 2-step conformational change model, neutralized HIV-1 in a PBMC assay.

TABLE 3

| MAb | Nominal Epitope (HR-2 peptide) | Env gp140 JRFL | Phospholipid Cardiolipin | Peptide-Lipid Conjugates | HIV Neutralization $ID_{50}$ in PBMC assay |
|---|---|---|---|---|---|
| 2F5 | ++ | ++ | + | 2-step conformational | 1 µg/mL |
| 98-6 | ++ | ++ | +++ | 2-step conformational | 3.5 µg/mL |
| 126-6 | + | ++ | +++ | Simple model | Non-Neut* |
| 167-D | + | ++ | ++ | Simple model | Non-Neut* |
| 13H11 | + | + | −ve | +/− | >50 µg/mL |
| 5A9 | + | + | −ve | +/− | >50 µg/mL |

*Corny et al, J. Virol. 74: 6168 (2000); Nyambi et al, J. Virol. 74: 7096 (2000)

All documents and other information sources cited above are hereby incorporated in their entirety by reference.

What is claimed is:

1. An immunogenic composition comprising a peptide comprising a HIV-1 gp41 2F5 epitope peptide having the amino acid sequence of ELDKWAS (SEQ ID NO:12) and a HIV-1 gp41 4E10 epitope peptide having the amino acid sequence WFNITNW (SEQ ID NO:21) and a linker, wherein the peptide is embedded in a liposome via the linker, wherein the liposome comprises an anionic lipid, and wherein the immunogenic composition does not have additional 4E10 or 2F5 epitope mimics besides SEQ ID NO:s 3, 5, 6, 7, 8, 9, 10, 11, 13, or 14.

2. The composition of claim 1, and wherein the liposome comprises POPC (1-Palmitoyl-2-Oleoyl-sn-Glycero-3-Phosphocholine).

3. The composition of claim 1, wherein the liposome comprises cholesterol.

4. The composition of claim 1, wherein the liposome comprises:

a. POPC, POPE (1-Palmitoyl-2-Oleoyl-sn-Glycero-3-Phosphoethanolamine), DMPA (1,2-Dimyristoyl-sn-Glycero-3-Phosphate), and cholesterol;

b. POPC and POPS (1-palmitoyl-2-oleoyl-sn-glycero-3-[phospho-L-serine]);

c. POPC, POPS, and lysoPC (lysophosphorylcholine);

d. POPC and POPE and sphingomyelin and cholesterol;

e. DOPC and cholesterol; or f. DPPC, DPPG and cholesterol.

5. The composition of claim 1, wherein the composition further comprises alum.

6. The composition of claim 1, wherein said composition further comprises lipid A, oCpG, or TLR agonist.

7. The composition of claim 1, wherein the anionic lipid is phosphatidylserine, phosphatidic acid, or cardiolipin.

8. The composition of claim 1, wherein the liposome comprises a sphingolipid.

9. The composition of claim 1, wherein the peptide embedded in the liposome binds an MPER neutralizing antibody.

10. The composition of claim 1, wherein peptide embedded in the liposome binds an MPER neutralizing antibody 2F5 or 4E10.

11. The composition of claim 1, wherein the composition further comprises an adjuvant.

12. The composition of claim 1, wherein the linker is GTH1.

13. The composition of claim 3, wherein the composition further comprises an adjuvant or alum.

14. The composition of claim 3, wherein the peptide embedded in the liposome binds an MPER neutralizing antibody.

15. The composition of claim 3, wherein the peptide embedded in the liposome binds an MPER neutralizing antibody 2F5 or 4E10.

16. The composition of claim 1, wherein the anionic lipid is a phospholipid.

* * * * *